United States Patent
Dakic et al.

(10) Patent No.: US 11,238,493 B1
(45) Date of Patent: *Feb. 1, 2022

(54) AUTOMATIC DATA INTEGRATION FOR PERFORMANCE MEASUREMENT OF MULTIPLE SEPARATE DIGITAL TRANSMISSIONS WITH CONTINUOUS OPTIMIZATION

(71) Applicant: DeepIntent, Inc., New York, NY (US)

(72) Inventors: Vaso Dakic, Irvine, CA (US); Sara He, New York, NY (US); Chris Paquette, New York, NY (US); Pavel Romanovski, Wallington, NJ (US); Jen Werther, Hillsdale, NJ (US); Anton Yazovskiy, Scotch Plains, NJ (US); Sourabh Gandhe, Maharashtra (IN); Chinmay Kulkarni, Maharashtra (IN); Nuupur Adathiya, Maharashtra (IN)

(73) Assignee: DeepIntent, Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 17/365,590

(22) Filed: Jul. 1, 2021

Related U.S. Application Data

(63) Continuation of application No. 17/182,200, filed on Feb. 22, 2021, now Pat. No. 11,055,737.

(51) Int. Cl.
  *G06Q 30/02* (2012.01)
  *G06N 20/00* (2019.01)
  (Continued)

(52) U.S. Cl.
  CPC ....... *G06Q 30/0246* (2013.01); *G06K 9/6256* (2013.01); *G06N 20/00* (2019.01);
  (Continued)

(58) Field of Classification Search
  CPC ........... G06Q 30/0246; G06Q 30/0243; G06N 20/00; G16H 10/60; G16H 20/10; G16H 80/00; G06K 9/6256
  (Continued)

(56) References Cited

U.S. PATENT DOCUMENTS

| | | | |
|---|---|---|---|
| 8,438,184 B1* | 5/2013 | Wang | H04L 67/306 |
| | | | 707/780 |
| 10,262,761 B1* | 4/2019 | Weintraub | G06Q 30/0242 |

(Continued)

OTHER PUBLICATIONS

Event Marketing in the Healthcare Industry (Year: 2020).*

(Continued)

*Primary Examiner* — Gautam Ubale
(74) *Attorney, Agent, or Firm* — Baker Botts L.L.P.

(57) ABSTRACT

In one embodiment, a method includes obtaining, from a demand-side platform (DSP), impression data specifying service providers and consumer tokens representing consumers who have received digital impressions of a set of advertising campaigns. A set of tokenized claims data records related to a prescription of a product is then received from a database server. A result set of integrated measurement records specifying measured campaigns linking the tokenized claims data records with impression data associated with consumer tokens and/or service provider identifiers is further received from the database server. Aggregated analytics reports based on the integrated measurement records are generated and presented. A machine learning model may be trained using a training dataset comprising features selected from the impression data and tokenized claims data records, to predict bid values or other parameters for use in updating, optimizing or modifying operation of the DSP for the original campaign or for other campaigns.

20 Claims, 13 Drawing Sheets

(51) Int. Cl.
  *G16H 10/60* (2018.01)
  *G16H 20/10* (2018.01)
  *G16H 80/00* (2018.01)
  *G06K 9/62* (2006.01)
(52) U.S. Cl.
  CPC ......... *G06Q 30/0243* (2013.01); *G16H 10/60* (2018.01); *G16H 20/10* (2018.01); *G16H 80/00* (2018.01)
(58) Field of Classification Search
  USPC ........................................ 705/14, 319, 14.45
  See application file for complete search history.

(56) References Cited

U.S. PATENT DOCUMENTS

| | | | | |
|---|---|---|---|---|
| 10,503,874 | B1* | 12/2019 | Leonardo | G16H 20/10 |
| 10,755,291 | B1* | 8/2020 | Sharma | G06Q 30/0254 |
| 11,113,707 | B1* | 9/2021 | Sharma | G06Q 30/0206 |
| 2011/0246310 | A1* | 10/2011 | Buchalter | G06Q 30/0275 |
| | | | | 705/14.71 |
| 2014/0019237 | A1* | 1/2014 | Gottfrid | G16H 20/10 |
| | | | | 705/14.52 |
| 2014/0278507 | A1* | 9/2014 | Potter | G06Q 30/0201 |
| | | | | 705/2 |
| 2014/0310063 | A1* | 10/2014 | Freeman | G06Q 30/0205 |
| | | | | 705/7.34 |
| 2014/0324447 | A1* | 10/2014 | Dittus | G06Q 30/0269 |
| | | | | 705/2 |
| 2014/0330575 | A1* | 11/2014 | Traughber | G16H 40/63 |
| | | | | 705/2 |
| 2015/0332283 | A1* | 11/2015 | Witchey | H04W 12/02 |
| | | | | 705/3 |
| 2016/0140587 | A1* | 5/2016 | Wilson | G06Q 30/0269 |
| | | | | 705/7.33 |
| 2019/0347697 | A1* | 11/2019 | Chalasani | G06N 7/005 |
| 2020/0160388 | A1* | 5/2020 | Sabeg | G06F 21/6254 |
| 2020/0363215 | A1* | 11/2020 | Rusignola | G05D 1/0088 |
| 2021/0005325 | A1* | 1/2021 | Perlman | G06F 16/24578 |
| 2021/0012326 | A1* | 1/2021 | Maxwell Zelocchi | |
| | | | | G06Q 20/3827 |
| 2021/0109795 | A1* | 4/2021 | Colombo | G06F 9/5044 |

OTHER PUBLICATIONS

Direct marketing in health and medicine: using direct mail, email marketing, and related communicative methods to engage patients (Year: 2020).*
Privacy in targeted advertising: A survey (Year: 2020).*
Sales promotion in health and medicine: using incentives to stimulate patient interest and attention (Year: 2020).*
The Limits of Empowerment—Role of mHealth Tools in the Healthcare Ecosystem (Year: 2019).*
Direct-to-Consumer Pharmaceutical Advertising (Year: 2011).*

* cited by examiner

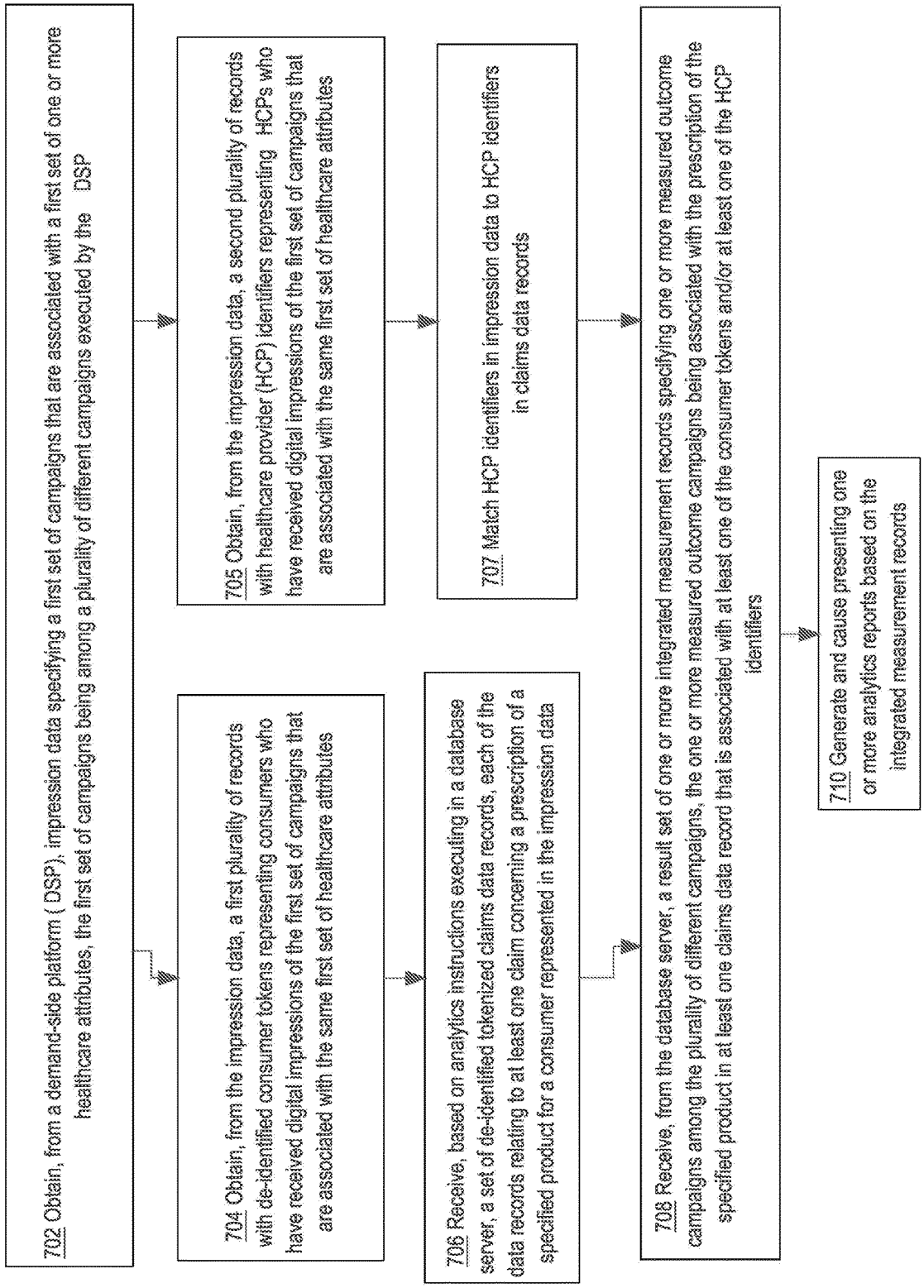

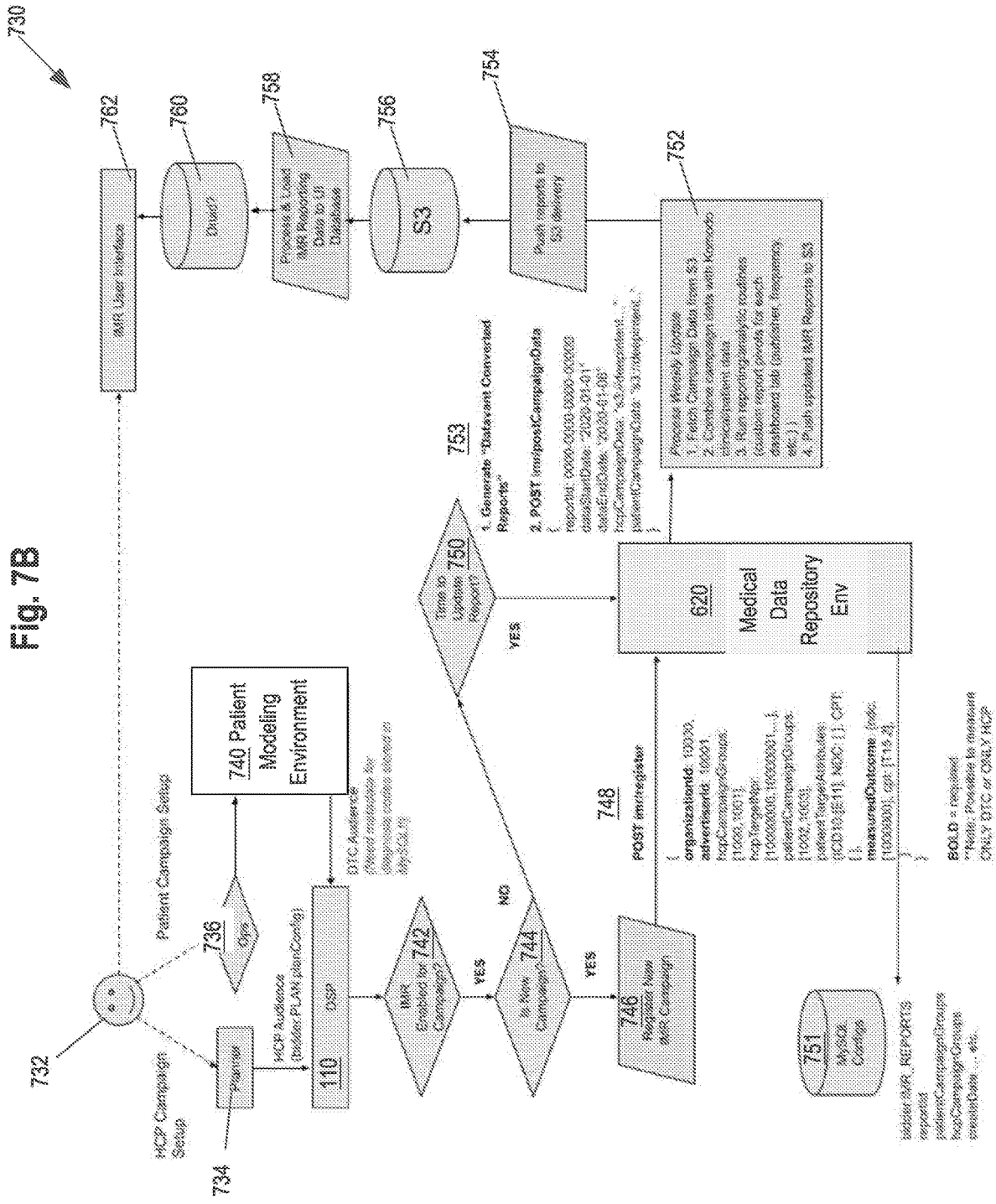

AUTOMATIC DATA INTEGRATION FOR PERFORMANCE MEASUREMENT OF MULTIPLE SEPARATE DIGITAL TRANSMISSIONS WITH CONTINUOUS OPTIMIZATION

BENEFIT CLAIM

This application claims the benefit under 35 U.S.C. 120 as a continuation of application Ser. No. 17/182,200, filed Feb. 22, 2021, the entire contents of which are hereby incorporated by reference as if fully set forth herein. Applicant hereby rescinds any disclaimer of claim scope in the application(s) of which the benefit is claimed and advises the USPTO that the present claims may be broader than any application(s) of which the benefit is claimed.

TECHNICAL FIELD

One technical field of the disclosure is computer implemented demand-side platform (DSP) systems, which are used in digital advertising technology. Another technical field is relational databases and specifically the use under stored program control of automatic joins of tables that store different datasets.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Digital advertising technology (ad tech) uses distributed computer systems under stored program control to determine what media or contents user computers are accessing, as well as what digital advertising units to select, transmit, or place in media, content, or other locations. Ad tech systems have developed sophisticated means for real-time bidding on the placement of electronic ad units within websites, mobile device feeds, and other applications. However, present ad tech systems still suffer from many limitations.

Many advertising agencies, pharmaceutical companies, medical equipment companies, insurance companies, and other healthcare related firms wish to enhance advertising impressions of healthcare products and services to applicable healthcare providers (HCPs) and consumers. Impression deployment may entail demand side platform (DSP) systems for targeted distribution of product information. Determining the appropriate online HCP identities and targetable consumers and where to deliver information regarding specific products and services may be challenging given the myriad types of medical conditions, HCPs and their practice histories, requirements for patient privacy under the Health Insurance Portability and Accountability Act (HIPAA), and the multitude of different products in the healthcare industry. Clinical medical data, prescribing behavior data, National Provider Identifier (NPI) data, demographic data, certification, appointment scheduling, payment data, and other information relating to an NPI is not generally accessible to agencies and advertisers for use in determining which HCPs would be the best fit for distributing information pertaining to particular products, or information pertaining to an NPI may not be fully comprehensive, or not coordinated with other data, and therefore limited in their utility. Thus, DSP systems often distribute product information to HCPs whose patients would not benefit from such distribution and/or omit distribution to many HCPs whose patients would benefit.

Data sellers often may sell data defining audience segments into a DSP. These approaches usually allow for only minimal customization of the audience to be targeted or cause significant delay in a customization that greatly reduces the relevance and rely on buckets or segments of cookie or device data that have been manually tagged to indicate a particular audience characteristic. Other data providers offer data via platforms which provide counts and aggregations for how many users with various attributes are recorded in a database of HCPs; these platforms do not have a DSP and thus require an intermediary to transfer audience data to a DSP. The lack of integration in this approach precludes providing HCP-specific reporting of engagement with advertisements in real-time. Furthermore, existing systems may use individual data stores based on browser cookie limitations and provide no sound way to unify digital identity data with third-party data to enable more real-time customization and relevancy of the advertisement.

Furthermore, existing technology provides no effective means to measure the effect of healthcare advertisements on patient results and provider behavior change as there is no effective means to digitally combine or join ad serving data with healthcare data (real-world evidence) and then, on an ongoing basis, customize and optimize the messaging based on campaign measurements of promotional response and/or near real-time clinical events. There are also no effective ways to measure the interactions between consumers and service providers and how certain advertisements lead to improved health results, including minimal ability to link offline behavior change to online campaign impression data. Integration of campaigns directed at HCPs and patients is impractical or does not exist. Even if this data could be determined, there is no practical or effective way to optimize DSPs or bids based on campaign measurements to account for the results.

SUMMARY OF PARTICULAR EMBODIMENTS

The appended claims may serve as a summary of the invention.

BRIEF DESCRIPTION OF THE DRAWINGS

FIG. 7A illustrates an example measurement and management process for a given campaign.

FIG. 7B illustrates an example measurement and management process for a given campaign.

DESCRIPTION OF EXAMPLE EMBODIMENTS

Figure 1:
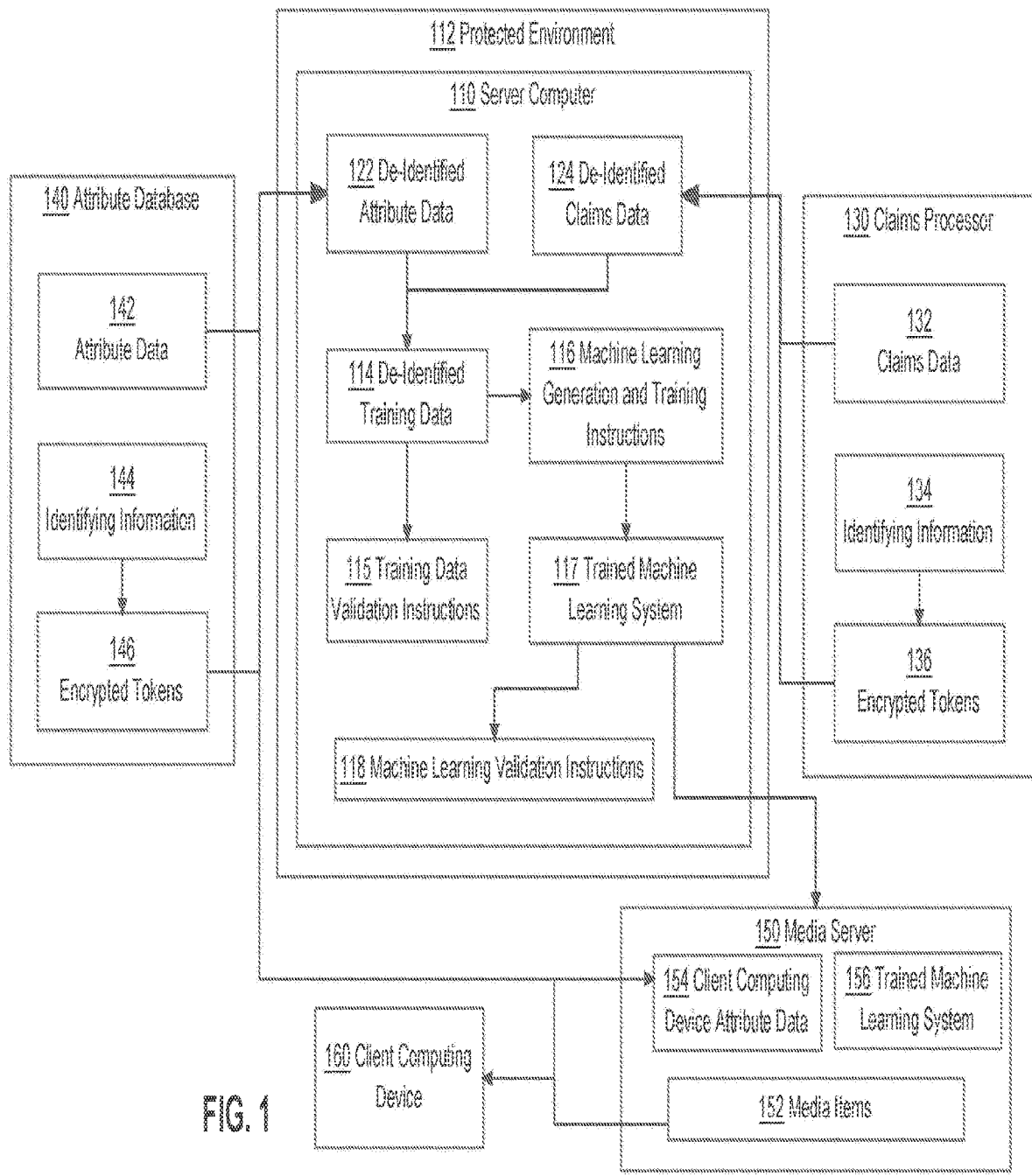
FIG. 1 depicts an example system for secure training and distribution of a machine learning system using protected data.

Example embodiments are described below in sections according to this outline:
1. GENERAL OVERVIEW
2. DIRECT-TO-CONSUMER MODELING
   2.1 STRUCTURAL EXAMPLE
   2.2 PROCESS OVERVIEW
   2.3 PROTECTED ENVIRONMENT IMPLEMENTATION
   2.4 MEDIA SERVER IMPLEMENTATION
   2.5 MODELING IMPLEMENTATION
   2.6 BENEFITS OF CERTAIN EMBODIMENTS
3. CAMPAIGN PERFORMANCE MEASUREMENT AND OPTIMIZATION
4. IMPLEMENTATION EXAMPLES
   4.1 HARDWARE OVERVIEW
   4.2 ARTIFICIAL NEURAL NETWORKS
5. EXTENSIONS AND ALTERNATIVES The embodiments disclosed herein are only examples, and the scope of this disclosure is not limited to them. Particular embodiments may include all, some, or none of the components, elements, features, functions, operations, or steps of the embodiments disclosed herein. Embodiments according to the invention are in particular disclosed in the attached claims directed to a method, a storage medium, a system and a computer program product, wherein any feature mentioned in one claim category, e.g. method, may be claimed in another claim category, e.g. system, as well. The dependencies or references back in the attached claims are chosen for formal reasons only. However, any subject matter resulting from a deliberate reference back to any previous claims (in particular multiple dependencies) may be claimed as well, so that any combination of claims and the features thereof are disclosed and may be claimed regardless of the dependencies chosen in the attached claims. The subject matter which may be claimed comprises not only the combinations of features as set out in the attached claims but also any other combination of features in the claims, wherein each feature mentioned in the claims may be combined with any other feature or combination of other features in the claims. Furthermore, any of the embodiments and features described or depicted herein may be claimed in a separate claim and/or in any combination with any embodiment or feature described or depicted herein or with any of the features of the attached claims.

1. General Overview

Computer systems used in healthcare marketing historically have relied on multiple different technologies to measure and optimize transmission of digital data including advertisements. Healthcare data is subject to latency and security considerations. Therefore, any existing common solutions for measuring effectiveness of online healthcare advertising campaigns have been disjointed and not integrated into a single media platform. Some measurement systems have long data refresh delays, questionable accuracy, insufficient transparency, and operate independently of the media platform. Additionally, changes to browser cross-domain tracking policies have introduced increasing challenges for third-party measurement solutions to measure campaigns. Consequently, healthcare marketers struggle to make real-time optimizations to their online campaigns based on offline health results data.

Furthermore, measuring the joint and mutual effect of integrated campaigns directed to service providers and directed to consumers has not been possible. An integrated campaign involves deliberate coordination of the delivery of advertisements to service providers and consumers with similar messaging. "Service provider," in one embodiment, may refer to a healthcare provider ("HCP"), and "consumer," in the same embodiment, may refer to a patient; however, other embodiments may be implemented with service providers in fields other than healthcare and with consumers other than patients, but also having privacy concerns. Integrated campaigns are valued in industry because they improve the common understanding of consumers and providers before an encounter such as an office visit. Evidence suggests that if a consumer and provider have received the same message concerning the safety of a drug or the efficacy of a drug, then more conversions will occur. A conversion, in this context, may comprise writing a prescription. Embodiments of the present disclosure provide the first distributed computer system or platform that is programmed to plan, activate, and measure integrated campaigns within a DSP, so that brands can run, measure, and optimize these campaigns all within a single platform. "DSP," in this context, refers to a demand-side platform or to an ad server computer, and all examples in this disclosure referring to "DSP" can be implemented using an ad server that does not act as a DSP, for example by publishers who serve ads but do not use DSPs.

Embodiments are structured to use medical claims data, which represents accurate accounting of healthcare activity, in compliance with legal regimes such as HIPAA that prevent the direct disclosure and use of personal health information for marketing uses. In embodiments, certain data is de-identified to protect privacy while allowing legal use for both advertising targeting and the measurement of campaign effectiveness.

In particular embodiments, ad serving data may be combined with healthcare data to measure the effect of healthcare advertisements on patient results and HCP behavior change. This combined data may further be used to measure interactions between the consumers and service providers who received those advertisements, and to quantify how certain ad campaigns lead to improved health results. A DSP thus offers the ability to plan, activate, and measure healthcare campaigns that deliver timely information to consumers and their service providers to help them make more informed decisions about their health. Measured results may then be used to adjust and optimize various parameters of particular ad campaigns in order to achieve a further desired result, thus enabling control, customization, and delivery of integrated campaigns for service providers and consumers.

In particular embodiments, a method includes, by a measurement server computer, obtaining, from a DSP, impression data specifying a first plurality of de-identified consumer tokens representing consumers who have received digital impressions of a first set of campaigns that are associated with a first set of one or more healthcare attributes. Impression data specifying a second plurality of HCP identifiers representing HCPs who have received digital impressions of the first set of campaigns that are associated with the first set of healthcare attributes is further obtained from the DSP. The first set of campaigns may be from among a plurality of different campaigns executed by the DSP. A set of de-identified tokenized claims data records is then received, based on analytics instructions executing in a database server; each data record may relate to at least one claim concerning a prescription of a specified product, and execution of these instructions may occur in a secure environment with data privacy safeguards. The method further includes receiving, from the database server, a result set of one or more integrated measurement records specifying one or more measured campaigns among the plurality of different campaigns. The one or more measured campaigns may be associated with the prescription of the specified product in at least one claims data record that is associated with at least one of the consumer tokens and/or at least one of the HCP identifiers. Finally, the method includes generating and causing presenting one or more analytics reports based on the integrated measurement records.

Certain technical challenges exist for running, measuring, and optimizing ad campaigns, such as those run by pharmaceutical companies. As one example, healthcare marketers often must rely on several different pieces of technology to run their digital ad campaigns. However, given the latency in healthcare data and the uniqueness of the challenges around managing consumer data, any solutions for measuring the effectiveness of a healthcare campaign are often disjointed and not fully integrated into a single media buying platform. Conventional measurement products may have long data refresh delays, questionable accuracy, and insufficient transparency, and they often operate independently of the media buying platform being used. Furthermore, another technical challenge exists in the lack of a platform that measures the joint and mutual effect of integrated campaigns for service providers and consumers. Yet another technical challenge lies in the fact that browser cross-domain tracking policies often introduce challenges for third-party measurement solutions seeking to measure the campaigns. Due to these limitations, healthcare marketers may struggle to make real-time optimizations to their campaigns based on offline health results data.

Certain embodiments disclosed herein may provide one or more solutions to address these challenges, as well as various technical advantages. As an example, the disclosed DSP may provide an integrated platform that enables the deliberate coordination of campaigns to target and deliver advertisements to select, relevant healthcare providers and consumers with similar messaging at appropriate times. For instance, the DSP may enable the delivery of key discussion points to an HCP and a patient prior to a clinical visit or interaction between the two that emphasize the efficacy of a particular drug. Such integrated campaigns may allow patients and providers to be 'synched' with relevant messaging concerning the particular drug ahead of their encounter/office visit. If a patient and HCP are both prepared to discuss the same message ahead of this interaction (such as the safety of the drug, its efficacy, etc.), this may result in a higher number of conversions among the patients.

This unified approach results in various technical advantages. As an example, one technical advantage of the embodiments may include the ability to run, manage, and measure integrated campaigns within a single, unified platform. Another technical advantage of the embodiments may include enabling entities to receive data representing interactions between qualified patients and HCPs and assess how influential their marketing campaigns are in driving conversions or changing patient behavior. Yet another technical advantage of the embodiments may include providing automated campaign optimization in response to this data in order to increase efficiency and targeting for future campaigns. Certain embodiments disclosed herein may provide none, some, or all of the above technical advantages. One or more other technical advantages may be readily apparent to one skilled in the art in view of the figures, descriptions, and claims of the present disclosure.

2. Direct-to-Consumer Modeling 2.1 Structural Example

FIG. 1 depicts an example system for secure training and distribution of a machine learning system using protected data. Server computer 110, claims processor 130, attribute database 140, media server 150, and client computing device 160 are communicative coupled over one or more networks. The network(s) broadly represent any combination of one or more data communication networks including local area networks, wide area networks, internetworks or internets, using any of wireline or wireless links, including terrestrial or satellite links. The network(s) may be implemented by any medium or mechanism that provides for the exchange of data between the various elements of FIG. 1. The various elements of FIG. 1 may also have direct (wired or wireless) communications links. The server computer 110, claims processor 130, attribute database 140, media server 150, client computing device 160, and other elements of the system each comprise an interface compatible with the network(s) and are programmed or configured to use standardized protocols for communication across the networks such as TCP/IP, Bluetooth, CAN protocol and higher-layer protocols such as HTTP, TLS, and the like.

Claims processor 130 comprises one or more computing systems configured to receive and store claims data. Claims processor 130 stores claims data 132 and identifying information 134. Claims data 132 comprises data identifying one or more status values for a plurality of personal data records. For example, claims data may comprise medical claims records identifying diagnosis codes, such as the International Statistical Classification of Diseases and Related Health Problems (ICD) codes, codes for procedures such as Current Procedural Terminology (CPT) codes, codes associated with healthcare providers (HCPs), Healthcare Common Procedure Coding System (HCPCS) codes, or J codes, or NDC codes for prescriptions. The status values may comprise existence or non-existence of specific codes, such as an ICD-10 code for a diagnosis of Type II diabetes. The claims data 132 may be associated with identifying information 134, such as names, addresses, birthdates, or other identifying information of a personal data record. Claims processor 130 uses the identifying information 134 to generate encrypted tokens 136 using the methods described herein. Claims processor 130 sends claims data 132 with encrypted tokens 136 to server computer 110. Additionally or alternatively, claims processor 130 may send the claims data 132 and identifying information 134 to a tokenization server which then generates the encrypted tokens 136 from the identifying information using the methods described herein and sends the encrypted tokens and claims data to server computer 110.

Attribute database 140 comprises a data store, such as a relational database or other structured data storage, configured to store attribute information for a plurality of personal data records. Attribute database 140 stores attribute data 142 and identifying information 144. Attribute data 142 may comprise individual values for a plurality of values. For example, attribute database 140 may store a plurality of rows, each of the plurality of rows corresponding to a different personal data record, and a plurality of columns, each of the plurality of columns corresponding to a different attribute. Attributes may include personal information such as age, physical activity level, weight, hair color, and/or eye color, data relating to an online search history, such as existence of particular search terms, websites visited, or other internet history, or data relating to one or more online accounts, such as social network accounts or other memberships. The attribute data 142 may be associated with identifying information 144 such as names, addresses, birthdates, or other identifying information of a personal data record. Attribute database 140 uses identifying information 144 to generate encrypted tokens 146 using the methods described herein. Attribute database 140 sends attribute data 142 with encrypted tokens 146 to server computer 110. Additionally or alternatively, attribute database 140 may send the attribute data 142 and identifying information 144 to a tokenization server which then generates the encrypted tokens 146 from the identifying information using the methods described herein and sends the encrypted tokens and attribute data to server computer 110.

Server computer 110 comprises one or more computing devices configured to generate and train one or more machine learning systems. Server computer 110 may be a physical server computer and/or a virtual server instance stored in a data center, such as through cloud computing. Server computer 110 may be configured to generate and train the machine learning system within protected environment 112. Protected environment 112 comprises a hardware or software environment which may include one or more server computers, such as server computer 110, one or more local networks, a load balancer, and/or data storage. Protected environment 112 is configured to protect data stored within the environment, such as through a firewall or other network security systems which restricts access through a network, such as the internet, to the various systems or devices within the protected environment. The protected environment 112 may be configured to not release data from the environment that does not meet certain criteria, as described further herein. In this manner, the protected environment may be used as a barrier to protect specific types of information, such as confidential information or restricted-use data, such as medical claims which are protected under HIPAA.

Server computer 110 stores de-identified attribute data 122 received from attribute database 140 and de-identified claims data 124 received from claims processor 130. The de-identified attribute data 122 and de-identified claims data 124 may comprise attributes and claims respectfully which are mapped to encrypted tokens but do not include any identifying information. Methods for generating the de-identified data are described further herein. Server computer 110 uses the de-identified attribute data 122 and de-identified claims data 124 to create de-identified training data 114 which server computer 110 stores. Server computer 110 further stores training data validation instructions 115, machine learning generation and training instructions 116, and machine learning validation instructions 118. De-identified training data 114 may be stored as a plurality of rows of data, each row corresponding to a different personal data record. The plurality of rows of data may include columns corresponding to different attributes of the personal data records and columns corresponding to status values, such as diagnosis codes, of the personal data records.

Training data validation instructions 115 comprise computer-readable instructions which, when executed by one or more processors of server computer 110, cause server computer 110 to determine whether a training dataset satisfies one or more criteria and perform a responsive action depending on whether the training dataset satisfies the one or more criteria. Machine learning generation and training instructions 116 comprise computer-readable instructions which, when executed by one or more processors of server computer 110, cause server computer 110 to generate a machine learning system based on one or more instructions and to train the machine learning system using de-identified training data 114. Machine learning validation instructions 118 comprise computer-readable instructions which, when executed by one or more processors of server computer 110, cause server computer 110 to determine whether a machine learning system satisfies one or more criteria and perform a responsive action depending on whether the training dataset satisfies the one or more criteria.

Computer executable instructions described herein may be in machine executable code in the instruction set of a CPU and may have been compiled based upon source code written in JAVA, C, C++, OBJECTIVE-C, or any other human-readable programming language or environment, alone or in combination with scripts in JAVASCRIPT, other scripting languages and other programming source text. In another embodiment, the programmed instructions also may represent one or more files or projects of source code that are digitally stored in a mass storage device such as non-volatile RAM or disk storage, in the systems of FIG. 1 or a separate repository system, which when compiled or interpreted cause generating executable instructions which when executed cause the computer to perform the functions or operations that are described herein with reference to those instructions. In other words, the drawing figure may represent the manner in which programmers or software developers organize and arrange source code for later compilation into an executable, or interpretation into bytecode or the equivalent, for execution by the server 110.

The server computer 110 uses machine learning generation and training instructions 116 and de-identified training data 114 to generate trained machine learning system 117. For example, the server computer 110 may generate a training dataset from the de-identified training data 114 based on one or more instructions and use the training dataset to train a machine learning system generated by the server computer based on one or more instructions. Server computer 110 sends the trained machine learning system 117 to the media server 150.

Media server 150 comprises one or more computers configured to send media to one or more client computing devices in response to a request. Media server 150 stores media items 152 and trained machine learning system 156 received from server computer 110. Media items 152 comprise one or more images, videos, or other media items that may be served to a client computing device. Media server 150 is configured to communicate with client computing device 160 to determine whether to send a media item of media items 152 to client computing device 160. Media server 150 determines whether to send a media item using client computing device attribute data 154 stored in media server 150.

Client computing device attribute data 154 comprises one or more attributes corresponding to the client computing device 160, such as attributes relating to a personal data record corresponding to the client computing device. Client computing device attribute data 154 may be received from client computing device 160, attribute database 140, and/or one or more other attribute sources. For example, the media server 150 may receive identifying information from client computing device 160 which the media server 150 sends to the attribute database 140 with a request for attribute data relating to client computing device 160.

While FIG. 1 depicts a single instances of server computer 110, attribute database 140, claims processor 130, media server 150, and client computing device 160 for the purpose of demonstrating a clear example, in some embodiments, the systems and devices in FIG. 1 may comprise a plurality of different systems or devices. For example, server computer 110 may comprise a plurality of server computers and/or external storage devices which store attribute data, claims data, training data, and/or any other data stored within protected environment 112. As another example, server computer 110 may communicate with a plurality of media servers 150, each of which may communicate with a plurality of client computing devices 160.

2.2 Process Overview

Figure 2:
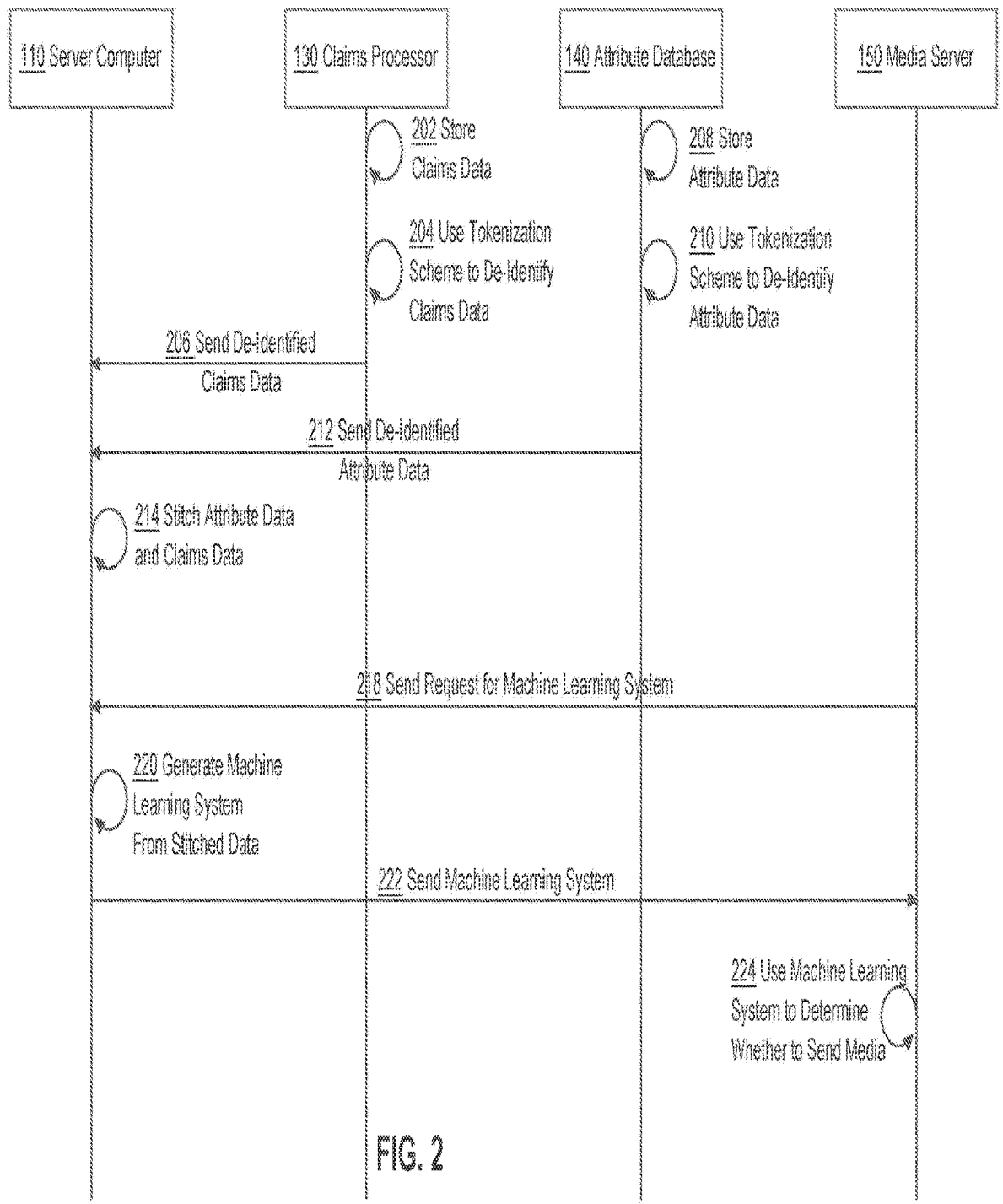
FIG. 2 depicts an example message diagram by which protected information is securely used to generate and train a machine learning system.

FIG. 2 depicts an example message diagram by which protected information is securely used to generate and use trained machine learning systems. FIG. 2 and other flow diagrams that are described herein may serve, alone or in combination with the descriptions of processes and functions in prose herein, as algorithms, plans or directions that may be used to program a computer or logic to implement the functions that are described. In other words, all the prose text herein, and all the drawing figures, together are intended to provide disclosure of algorithms, plans or directions that are sufficient to permit a skilled person to program a computer to perform the functions that are described herein, in combination with the skill and knowledge of such a person given the level of skill that is appropriate for inventions and disclosures of this type.

At step 202, claims processor 130 stores claims data. Claims data, as used herein, refers to status value data for one or more personal data records. Personal data records, as used herein, refer to a record of an individual with one or more values relating to said individual. Thus, an individual claims data record may identify a status of an individual as well as identify the individual through identification information, such as a name, birthdate, social security number, address, or other identifying information. The status of the individual may include a medical status, personal status, legal status, or any other data value relating to a status which may be stored in claims data records. For example, an individual claims data record may include a medical diagnosis from a medical professional. An example claims processor may comprise an intermediary between medical professionals and insurance agents, thus receiving medical records comprising protected data, such as diagnoses or prescriptions, which are then routed to insurance agents.

At step 204, claims processor 130 uses a tokenization scheme to de-identify the claims data. For example, the claims processor may create a data token by hashing specific pieces of identifying information, such as first name, last name, zip code, and date of birth, using a particular hash function and encrypting the hashed information. The claims processor may then create de-identified claims data comprising the data token and one or more status data values for the data token. As a practical example, if a claims data record comprised a full name, zip code, date of birth, and medical diagnosis for a personal data record, the claims processor 130 may generate the token using the identifying information and store a de-identified data record comprising the token and the medical diagnosis. As the token is generated from identifying information for a personal data record, the token is unique for each personal data record. While the disclosure describes a data token generated through hashing of identifying information and encryption of the hashed information, any identifying algorithmic scheme for generating a unique data token from identifying information may be used.

At step 206, claims processor 130 sends de-identified claims data to server computer 110. For example, claims processor 130 may send the plurality of tokens and corresponding status values for each of the plurality of tokens to server computer 110 which server computer 110 stores as de-identified claims data. Claims processor 130 may send the de-identified claims data as a plurality of data records, each of which comprising a unique token but not including any identifying information.

At step 208, attribute database 140 stores attribute data. Attribute data, as used herein, refers to a plurality of attribute data values for one or more personal data records. Thus, an individual attribute data record may identify a plurality of attributes of an individual as well as identify the individual through identification information, such as a name, birthdate, social security number, address, or other identifying information. Attributes may include known information relating to personal data records, such as personal information, internet history information, account information, or other stored information. In embodiments, attribute database 140 may store data relating to hundreds of attributes with data records containing information relating to a subset of the hundreds of attributes, such as when attribute data is unavailable for a particular personal data record for one or more of the attributes.

At step 210, attribute database 140 uses a tokenization scheme to de-identify the attributed data. In an embodiment, the tokenization scheme used by attribute database 140 to de-identify the attribute data is the same tokenization scheme used by claims processor 130 to de-identify the claims data. For example, if the tokenization scheme used by the claims processor involved using a particular hash function to hash a string comprising a first name, last name, and zip code and encrypting the hashed string using a particular encryption key, the tokenization scheme used by attribute database 140 may also use the particular hash function to hash the same string and encrypt the same hashed string using the same particular encryption key. In this manner, despite both claims processor 130 and attribute database 140 de-identifying information separately, the same token is created by both claims processor and attribute database 140 for the same personal data record. Additionally or alternatively, the tokenization may be provided by a tokenization server which uses the same method to generate tokens for claims processor 130 and attribute database 140. Attribute database 140 may then create the de-identified attribute data comprising, for each personal data record, a token and values for one or more of the attributes.

At step 212, attribute database 140 sends de-identified attribute data to server computer 110. For example, attribute database 140 may send the plurality of tokens and corresponding attribute values for each of the plurality of tokens to server computer 110 which server computer 110 stores as de-identified attribute data. Attribute database 140 may send the de-identified attribute data as a plurality of data records, each of which comprising a unique token but not including any identifying information.

At step 214, server computer 110 stitches attribute data and claims data into a stitched data set. For example, server computer 110 may generate a plurality of rows of data, each row corresponding to a particular personal data record. One example of a stitching technique may comprise a left join of the claims data to the attribute data, thereby keeping all attribute data but only storing, in the de-identified training data, claims data stored with a token that corresponds to a token of the attribute data. As another example, server computer 110 may identify claims data comprising a particular token and attribute data comprising the same particular token. Server computer 110 may generate a row of data for the particular token, the row of data comprising a plurality of columns for a plurality of attributes based on the attribute data and one or more columns for one or more status values based on the claims data. Thus, while each row comprises attribute data for a personal data record and claims data for the personal data record, the rows do not include identifying information for the personal data record.

While the systems and methods described in reference to FIG. 1 include the tokenization of identifying information, in other embodiments, the identifying information may not be tokenized and/or encrypted. For example, claims data 132, identifying information 134, attribute data 142, and identifying information 144 may be sent directly to the server computer where the server computer, in the protected environment stitches together the two datasets using the identifying information instead of using the encrypted tokens to match claims data to attribute data.

At step 218, media server 150 sends a request to server computer 110 for a machine learning system. The request may be sent through an application programing interface of the server computer 110 and may comprise identifications of input columns and output columns from the stitched data. For example, the request may identify a subset of the plurality of attributes to be used as inputs and existence of a particular status value as an output. The request may additionally include parameters for the machine learning system, such as number of nodes or layers.

At step 220, server computer 110 generates a machine learning system from the stitched data based on the request. For example, the server computer 110 may generate a machine learning system, such as a random forest model, neural network, logistic regression, or gradient boosted decision tree such as the XGBoost algorithm, using stored parameters and/or parameters received from media server 150. The server computer 110 may then train the machine learning system using the attributes identified by media server 150 as inputs and a status value for a particular status as an output.

As a practical example, media server computer may identify five input attributes of age, gender, average number of checkups, weight, and height and an output status value indicating existence or non-existence of a diabetes diagnosis. Server computer may identify corresponding columns of the attribute data and claims data and generate a training dataset using only those columns. Additionally or alternatively, the server computer may generate a column where data in the column is non-numerical or stored in a different manner. For example, if a status value column stored at server computer 110 includes, for each row, one or more diagnosis codes for diagnoses corresponding to a personal data record, the server computer 110 may generate a column for a particular diagnosis code by including, in each row of the column, a '0' value if the row did not include the particular diagnosis code and a "1" if the row did include the particular diagnosis code.

At step 222, server computer 110 sends the machine learning system to media server 150. In an embodiment, server computer 110 validates one or more of the training dataset used to train the machine learning system or the trained machine learning system using the methods described herein prior to sending the machine learning system to media server 150. The trained machine learning system may be sent in a form that is readily usable by media server 150, such as a matrix of weights for the machine learning system.

At step 224, media server 150 uses the machine learning system to determine whether to send media to a client computing device. For example, media server 150 may receive attribute data for the client computing device. The attribute data may include values for each attribute that was used to train the machine learning system. Media server 150 may use the machine learning system to compute, from the attribute data for the client computing device, a likelihood of existence of the status. Based on the likelihood of existence of the status, media server 150 may send a related media item to the client computing device. For example, media server 150 may determine whether the likelihood is greater than a threshold value and, if the likelihood is greater than the threshold value, send the media item to be displayed on the client computing device.

Furthermore, in an embodiment, after step 214, 224, or other points in the process, input may be received to request one or more analytic reports based upon the results of preceding steps. Examples of reports that may be requested and generated at points within the process flow of FIG. 2 are described herein in other sections in connection with FIG. 8, FIG. 9.

2.3 Protected Environment Implementation

Figure 3:
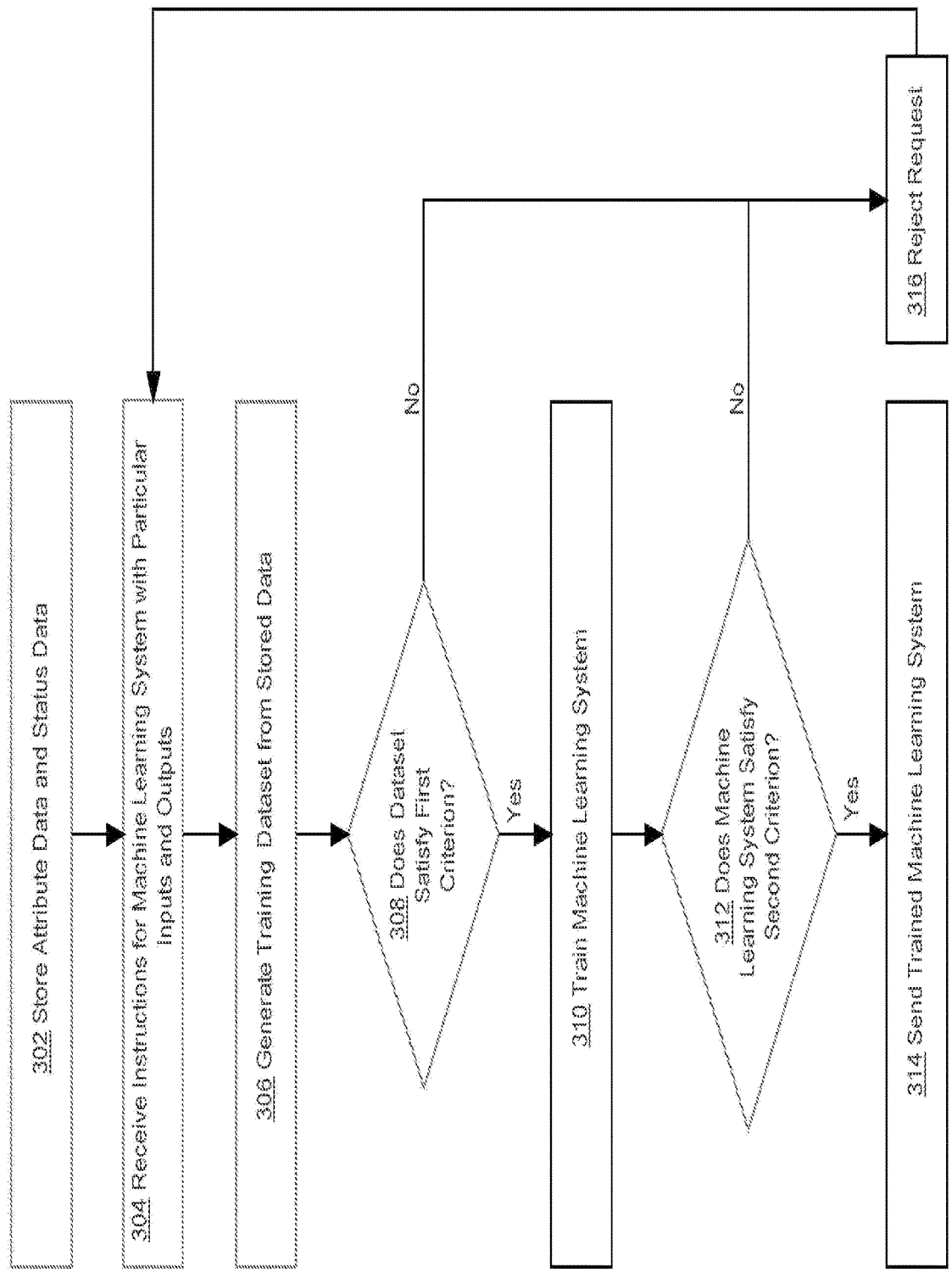
FIG. 3 depicts an example method for building and validating a machine learning system in a protected environment.

FIG. 3 depicts an example method for building and validating a machine learning system in a protected environment.

At step 302, a server computer within a protected environment stores attribute data and status data. For example, the server computer may store a plurality of columns of data, each column corresponding to a different attribute with values in each row indicating an attribute value for a particular personal data record. The server computer may additionally store one or more columns of data identifying status values, such as ICD-10 codes.

At step 304, the server computer receives instructions to generate a machine learning system with particular inputs and outputs. The instructions may identify which attributes to use as inputs and presence or absence of a status value as an output. For example, instructions may specify inputs as age, gender, weight, and height and an output as presence or absence of the ICD-10 code for Type 2 Diabetes. The instructions may also identify parameters for the machine learning system, such as a number of layers or number of nodes. Additionally or alternatively, the server computer may store parameters for the machine learning system and/or be configured to vary parameters for the machine learning system in response to the machine learning system failing to satisfy one or more criteria.

At step 306, the server computer generates a training dataset from stored data. For example, the server computer may initially identify personal data records that have values for each of the selected inputs. For example, some personal data records may lack a value for 'age' or 'gender' and may thus not be used to generate a training dataset if the instructions identified age and gender as inputs. The server computer may generate a training dataset for a plurality of personal data records with attribute values set as inputs and existence or non-existence of a status value as the output. For example, if the output was specified as existence of a particular ICD-10 code, then outputs for personal data records which included the particular ICD-10 code may be set to 1 while outputs for personal data records which did not include the particular ICD-10 code may be set to 0.

In an embodiment, generating the training dataset comprises selecting a subset of the stored data which could be used to generate the training dataset. For example, if three thousand data records include the required attributes, the server computer may select less than the three thousand data records to train the machine learning system. The number of records used may be identified in the received instructions and/or may be a stored percentage value. For instance, the server computer may be configured to only use half of the available records. Additionally or alternatively, the server computer may select records such that a minimum number of records with the output are used for training and a minimum number of records with the records are not used for training, thereby ensuring that the machine learning system is unable to memorize all stored personal data records.

At step 308, the server computer determines whether the dataset satisfies a first criterion. The first criterion may comprise a minimum number of instances of a positive value for the output. The server computer may be configured to determine whether there are at least a threshold number of instances of personal data records with the status value as an output. For example, if the output value is a particular ICD-10 code, the server computer may determine if at least a threshold number of data records in the stored data which can be used to build the training dataset comprise the particular ICD-10 code. The threshold number may be a value stored at the server computer or identified in the received instructions. The first criterion may additionally or alternatively include a minimum number of instances of personal data records without the status value as an output, a minimum and/or maximum ratio between personal data records with the status value as an output and data records without the status value as an output, and/or a minimum number of remaining data records that were not used in the generation of the training dataset that include the status value and/or do not include the status value.

Step 308 may be performed before the generation of the training dataset, thereby determining whether a training dataset generated from the stored data could satisfy the first criterion. For example, if the first criterion is a minimum number of instances of a particular ICD-10 code, the server computer may initially identify each data record which could be used to generate the training dataset and determine whether a number of the data records meets or exceeds the minimum number. In an embodiment, the server computer determines whether the stored data includes the minimum number of instances of the status value generally in addition to determining whether the stored data which could be used to build the training dataset includes the minimum number of instances of the status value. Thus, the server computer may distinguish between whether any training dataset could meet the first criterion when using the identified status value as an output or whether a training dataset using the requested attributes as inputs could meet the first criterion when using the identified status value as an output.

If the dataset does not satisfy the first criterion, at step 316 the server computer rejects the request for a machine learning system. For example, the server computer may send data to a requesting computing device rejecting the request for the machine learning system. The rejection may state that the first criterion was not satisfied. In an embodiment, the rejection additionally identifies whether the first criterion could be satisfied with different inputs, such as when a minimum number of instances of the output status value exists but does not exist in records which comprise attribute values for the requested inputs.

If the dataset does satisfy the first criterion, at step 310 the server computer trains a machine learning system using the training dataset. For example, the server computer may generate a new machine learning system using received and/or stored values for the parameters of the machine learning system. The machine learning system may comprise a logistic regression model, neural network, random forest model, gradient boosted decision tree, and/or any machine learning system which can be used to solve a classification problem. In an embodiment, the received instructions specify a type of machine learning system to train from a plurality of types of machine learning systems. For example, the server computer may store instructions for generating any of a plurality of machine learning systems. The server computer may receive instructions specifying which of the plurality of machine learning systems to generate and train. The server computer may generate the machine learning system using stored parameters and/or received parameters and train the machine learning system using attributes for personal data records as inputs and a value indicating existence or non-existence of a particular status as outputs.

At step 312, the server computer determines whether the machine learning system satisfies a second criterion. The second criterion may relate to an accuracy of the machine learning system, thereby ensuring that the machine learning system is unable to memorize inputs completely. For example, the second criterion may be a maximum average computed percent chance of the status value when using the machine learning system to compute outputs for the input training datasets which included the status as an output.

In an embodiment, the second criterion comprises a minimum fraction of population at risk based on the machine learning system. For example, the server computer may use the trained machine learning system to compute outputs for a plurality of input datasets. The input datasets may include datasets generated from stored data that was not used to train the machine learning system, datasets that were used to train the machine learning system, and/or datasets received with the initial instructions to generate and train the machine learning system. The server computer may then compute a fraction of population at risk based on a number of positive outputs from the plurality of input datasets and/or a number of instances in the training dataset of a positive status value. An example equation may comprise:

$$R = T/P$$

where R is the fraction of the population at risk, T is the number of instances in the training dataset of a true positive for the output value, and P is the number of positive predictions from using the machine learning system on the plurality of input datasets. The server computer may store a maximum threshold value for R as the second criterion, such as 0.2. Thus, if R is greater than 0.2, the server computer may determine that the machine learning system does not satisfy the second criterion.

If the machine learning system does not satisfy the second criterion, at step 316 the server computer rejects the request for a machine learning system. For example, the server computer may send data to a requesting computing device rejecting the request for the machine learning system. The rejection may state that the second criterion was not satisfied. In an embodiment, the server computer, after sending the rejection, may receive another request to generate a machine learning system. If the rejection was received based on the first criteria, the server computer continues with step 306. If the rejection was received based on the second criteria and the selected inputs and outputs remained the same, the server computer may skip checking the first criteria which is known to be satisfied. For example, the second request may specify the same inputs and outputs, but vary the parameters for training the machine learning system in an attempt to decrease its accuracy or the percentage of the population at risk. The server computer may generate a new machine learning system with the new parameters, train the new machine learning system with the same training dataset, and determine whether the new machine learning system satisfies the second criterion.

If the machine learning system satisfies the second criterion, at step 314 the server computer sends the trained machine learning system to the requesting computing device. For example, the server computer may release the trained machine learning system from the protected environment to the requesting device in response to determining that all criteria have been satisfied. The trained machine learning system may comprise weight values for each of the columns without including any of the training data used to create the trained machine learning system, thereby providing protection of personal data while still providing a machine learning system trained based on the personal data. As the server computer is configured to perform these tasks without allowing any external access to the data stored in the server computer, the server computer provides a means for utilizing protected or personal information without providing any knowledge of the protected or personal information.

2.4 Media Server Implementation

Figure 4:
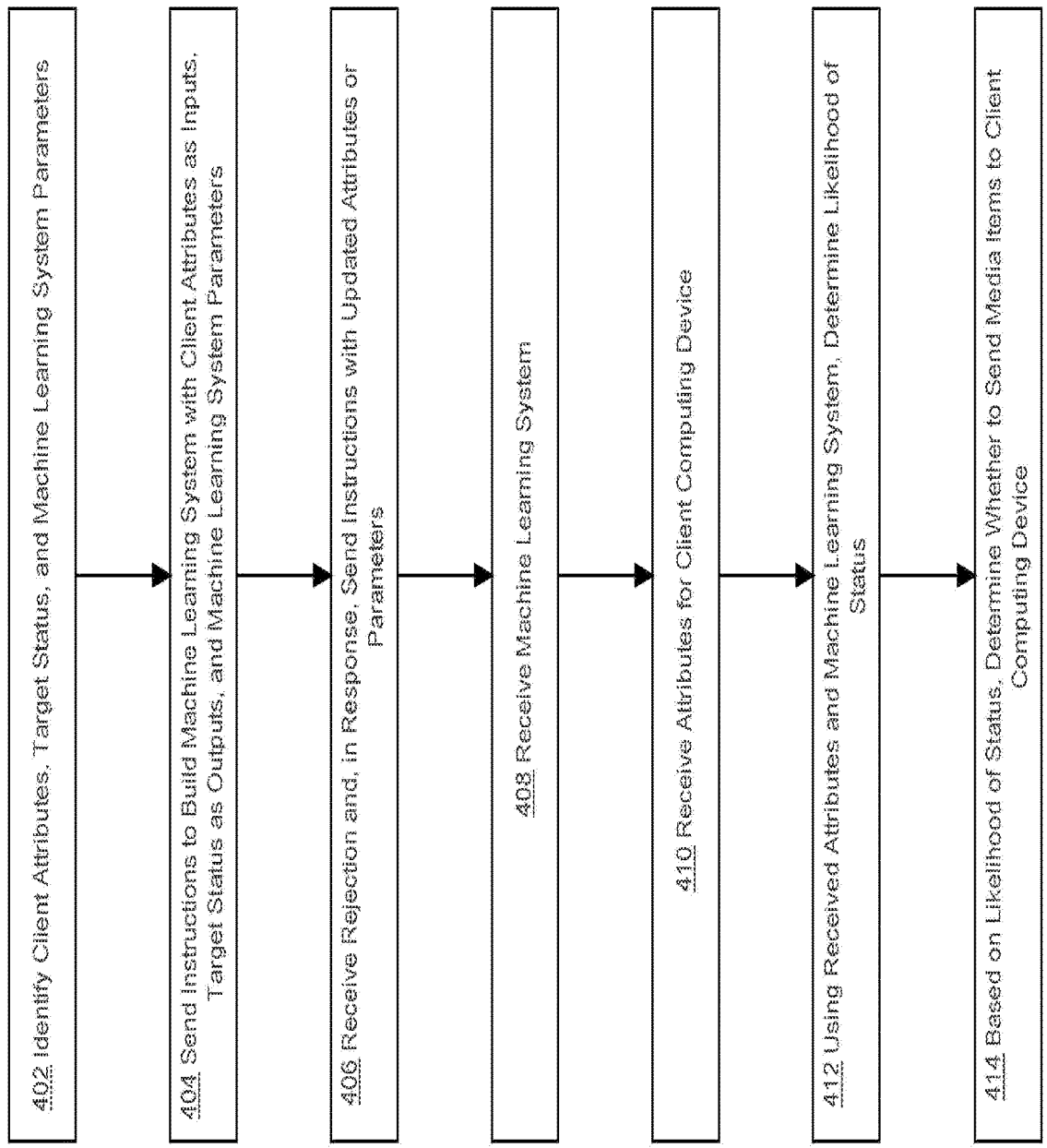
FIG. 4 depicts an example method for utilizing a secure environment to build and validate machine learning systems.

FIG. 4 depicts an example method for utilizing a secure environment to build and validate machine learning systems.

At step 402, a media server identifies client attributes, a target status, and machine learning system parameters. For example, the media server may receive input specifying client attributes for inputs and a target status as the output. The media server may additionally receive input specifying the machine learning parameters. Additionally or alternatively, the media server may store initial machine learning parameters. In an embodiment, the media server further receives input specifying a type of machine learning system to build.

At step 404, the media server sends instructions, to a secure environment, to build a machine learning system with the identified client attributes as inputs, target status as outputs, and the machine learning system parameters. For example, the media server may send instructions through an API of a server computer executing the secure environment to build a machine learning system, the instructions identifying the attributes to use as inputs and the status value to use as the output.

At optional step 406, if the media server receives a rejection, the media server, in response, sends instructions with updated attributes or parameters. The media server may receive a rejection if training data or the machine learning system failed to meet one or more criteria. The media server may cause display of an error message and request different inputs, outputs, and/or parameters to send to the server computer. In an embodiment, the media server may be configured to vary parameters for the machine learning system when an error is received based on the machine learning system failing to meet one or more criteria. For example, the media server may be configured to change a number of nodes or a number of layers pseudo-randomly and/or based on a stored second set of parameters.

At step 408, the media server receives a trained machine learning system. For example, the media server may receive the trained machine learning system from the secure environment when the machine learning system has satisfied stored criteria. The media server may store the machine learning system and identifiers of the attributes used as inputs and status used as the output for the machine learning system.

At step 410, the media server receives attributes for a client computing device. The media server may be configured to determine whether to serve a particular media item to the client computing device. For example, the media server may be configured to determine which computing devices to send an advertisement for a diabetes medication. The media server may receive the attributes for the client computing device prior to the steps 402-408 or after. For example, the media server may store attributes for a plurality of client computing devices prior to receiving a request for media to be sent to the client computing device.

Additionally or alternatively, the media server may request attribute data from an outside source, such as an attribute database, based on information received from the client computing device. For example, the media server may receive a request to display media on a client computing device, such as in response to a client computing device navigating to a particular webpage. The media server may additionally receive data from the client computing device or from an external source which the media server may send to the attribute database with a request for attributes of the client computing device. The request may specify the attributes used to train the machine learning system.

At step 412, the media server uses received attributes and the machine learning system to determine a likelihood of a status. The media server may use the attributes as inputs into the machine learning system to compute a result or goal value indicating a likelihood of the status. Thus, if the machine learning system was trained using a diagnosis of Type 2 Diabetes as the output, the media server may use the attributes to compute a likelihood of Type 2 Diabetes based on the input attributes. The server computer may compute the likelihood of the status in response to receiving a request for media and/or in advance of receiving the request. For example, the server computer may compute likelihoods for a plurality of client computing devices and store the likelihood values to be used later.

In an embodiment, the media server performs steps 402-412 a plurality of times for a single client computing device. For example, the media server may request a plurality of machine learning systems from a protected environment, each trained with a different status value as the output. The media server may use the plurality of trained machine learning systems to compute a plurality of likelihood values, each corresponding to a different status. The media server may store the plurality of likelihood values for use in determining which media item to send to a client computing device.

At step 414, based on the likelihood of the status, the media server determines whether to send media items to the client computing device. For example, the media server may store a media item corresponding to a particular status. The media server may determine whether the likelihood of the status for the client computing device is greater than a stored threshold value, such as 80%. If the likelihood is greater than the stored threshold value, the media server may send the media item to the client computing device. If the likelihood is not greater than the stored threshold value, the media server may send a different media item to the client computing device.

In an embodiment, the media server selects one of a plurality of media items based on a plurality of likelihood values. For example, the media server may store a plurality of media items, each corresponding to one or a plurality of statuses. The media server may use a plurality of machine learning systems, each trained with one of the plurality of statuses as an output, to compute a plurality of likelihoods of a status for the client computing device. The media server may identify the status with the highest likelihood and select the media item corresponding to the identified status. The media server may then send the selected media item to the client computing device.

In an embodiment, the media server uses the likelihood of the status to determine a value for one or more media items. For example, the media server may receive a request to send a plurality of media items, such as one thousand media items, to client computing devices corresponding to personal data records with the status value. If the likelihood of the status for a particular personal data record is 50%, the media server may value sending the media item to the client computing device as being valued as one half of a personal data record corresponding to the status. Thus, if the request was for one thousand media items to be sent to client computing devices corresponding to personal data records with the status value, the media server may send media items to client computing devices until a value of personal data records sent corresponds to one thousand, such as two thousand media items being sent to client computing devices corresponding to personal data records with a 50% likelihood of the status value. Additionally or alternatively, the media server may use the likelihood of the status to dynamically price sending media items to client computing devices. For example, if a price for sending a media item to a client computing device corresponding to a personal data record with the status value is $10, the media server may charge $5 for sending the media item to a client computing device corresponding to a personal data record with a 50% likelihood of the status value.

2.5 Modeling Implementation

In an embodiment, the systems and methods described herein may be used to identify effects of particular actions on a status of a personal data record while protecting the used information. For example, the server computer may determine, within the protected environment, a percentage of identified personal data records with a particular status or a percentage of identified personal data records which received a benefit based on a request from an external computing device, such as the media server. Embodiments are described further herein.

In an embodiment, the server computer determines a percentage of identified personal data records with a particular status. For example, after sending media items to a plurality of client computing devices, the media server may store identifiers for a plurality of personal data records corresponding to computing devices which received media items corresponding to a particular status, such as cookie identifiers. The media server may send to the server computer, the identifiers and an identification of the particular status. In an embodiment, the media server generates unique tokens for the plurality of personal data records using the methods described herein and sends the generated unique tokens to the server computer with an identification of the status. The server computer may match the received identifiers to personal data records stored in the protected environment, such as through a mapping of cookie identifiers to personal data records. The server computer may then determine, within the protected environment, for each identifier, whether the identifier corresponds to the particular status. As an example, the server computer may determine whether a particular ICD-10 code is listed in a row corresponding to the personal data record. The server computer may determine a number and/or percentage of identifiers that correspond to the particular status and send the number and/or percentage to the media server.

In an embodiment, the server computer may be configured to only send the number or percentage of identifiers from the protected environment in response to determining that the number and/or percentage satisfies a third criterion. The third criterion may be a minimum number of total identifiers, a maximum number and/or percentage of identifiers with the particular status, or a minimum number or percentage of identifiers with the particular status. By using a third criterion, the server computer may ensure that protected information is not released to the media server.

In an embodiment, the server computer is configured to determine a benefit for one or more personal data records based on additional received claims data. For example, the claims processor may send additional claims data to the server computer. The server computer may receive the additional claims data and correlate the additional claims data with previously stored claims data, such as through unique identifiers generated by the claims processor. The server computer may additionally receive data from the media server comprising a plurality of identifiers of personal data records corresponding to computing devices which received a media item corresponding to a particular status. The server computer may determine, from the plurality of identifiers of personal data records and the received additional claims data, a number and/or percentage of personal data records which received a benefit. A benefit, as used herein, comprises a determination made by the server computer of a change in a status of a personal data record that has been defined as beneficial. Definitions used by the server computer as a "benefit" are further described herein.

In an embodiment, a benefit is defined as an additional status corresponding to the personal data record. For example, the server computer may receive an identification, from the media server, of a prescription code for a medication corresponding to a sent media item. The server computer may determine, from the additional claims data, whether any of the personal data records corresponding to the identifiers received from the media server comprise the prescription code for the medication. The server computer may compute a number and/or percentage of the identifiers which correspond to personal data records that comprise the prescription code in the additional claims data and send the number and/or percentage to the media server.

A benefit may also be defined as removal or change of a status in corresponding data records. For example, the server computer may be configured to determine a benefit has occurred if the particular status is listed as removed in future data records, has been changed to a status identified by the media server, such as a less severe version of a disease, or if a different status, such as a prescription for a pain medication, has been removed, thereby indicating that pain management is no longer necessary. In an embodiment, the benefit may be defined by a number of claims, such as a decrease in a number of doctor visits or a decrease in refills of a prescription.

In an embodiment, the benefit is defined by a request from the media server. For example, the media server may send a request to the server computer comprising a plurality of identifiers and one or more statuses and/or status changes for the plurality of identifiers. As a practical example, the media server may send a request for identification of a number and/or percentage of identifiers sent by the media server that correspond to personal data records which had a removal of a particular status in additional claims data. The server computer may identify, of the identifiers sent by the media server, each identifier that initially corresponded to the particular status. The server computer may then identify, of the identifiers that corresponded to the particular status, which identifiers had a removal of the particular status in the future claims data. The server computer may then send a number or percentage of received identifiers that had the removal of the particular status in future claims to the media server.

2.6 Benefits of Certain Embodiments

The systems and methods described herein contribute to the technical character of machine learning system use by being particularly adapted to a specific technical implementation where instructions to generate a training dataset and machine learning system and to train said machine learning system using the training dataset are received from an external server computer. Meanwhile, the server computer within the protected environment is used to train and validate the machine learning system which is then released from the protected environment to be used by the external computing system. This unique technical implementation of machine learning systems provides additional data protections for information stored by the server computer by performing the training and validations in the server computer in a manner where the initial training data cannot be viewed by a user of an external device.

The systems and methods described herein further provide a practical application of a machine learning system through the generation and training of the machine learning system in a protected environment in a server computer. These systems and methods provide a particular means of solving a technical problem, the use of protected information without providing said protected information into an environment where it can be seen or used by a user. By using stored rules to validate the machine learning system in the protected environment and providing a means for defining the generation and training of the machine learning system from outside the environment and without access to the training data, the systems and methods described herein provide a technical solution to a technical problem of how to provide a trained machine learning system which protects training data without providing access to said training data.

3. Campaign Performance Measurement and Optimization

In particular embodiments, ad serving data may be combined with healthcare data at a measurement server computer to measure the effect of healthcare advertisements on patient results and HCP behavior change. This combined data may further be used to measure interactions between consumers and service providers, and to quantify how certain ad campaigns lead to improved health results. A DSP thus offers the ability to plan, activate, and measure healthcare campaigns that deliver timely information to patients and their HCPs to help them make more informed decisions about their health. Measured results may then be used to adjust and optimize various parameters of particular ad campaigns in order to achieve a further desired result, thus enabling control, customization, and delivery of independent or integrated campaigns for HCPs and patients.

Figure 6A:
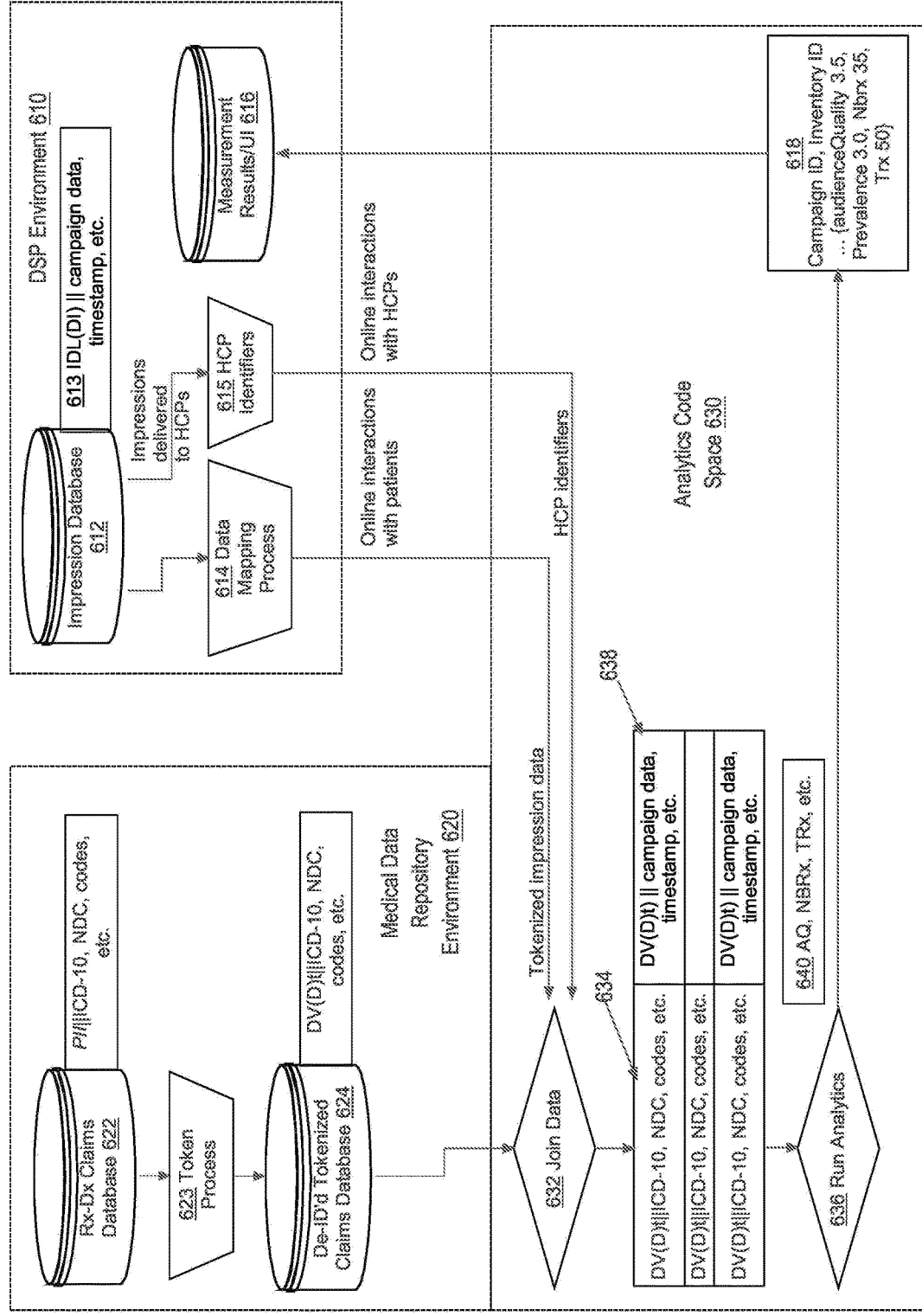
FIG. 6A illustrates an example distributed computer system with which certain embodiments may be implemented.
Figure 6B:
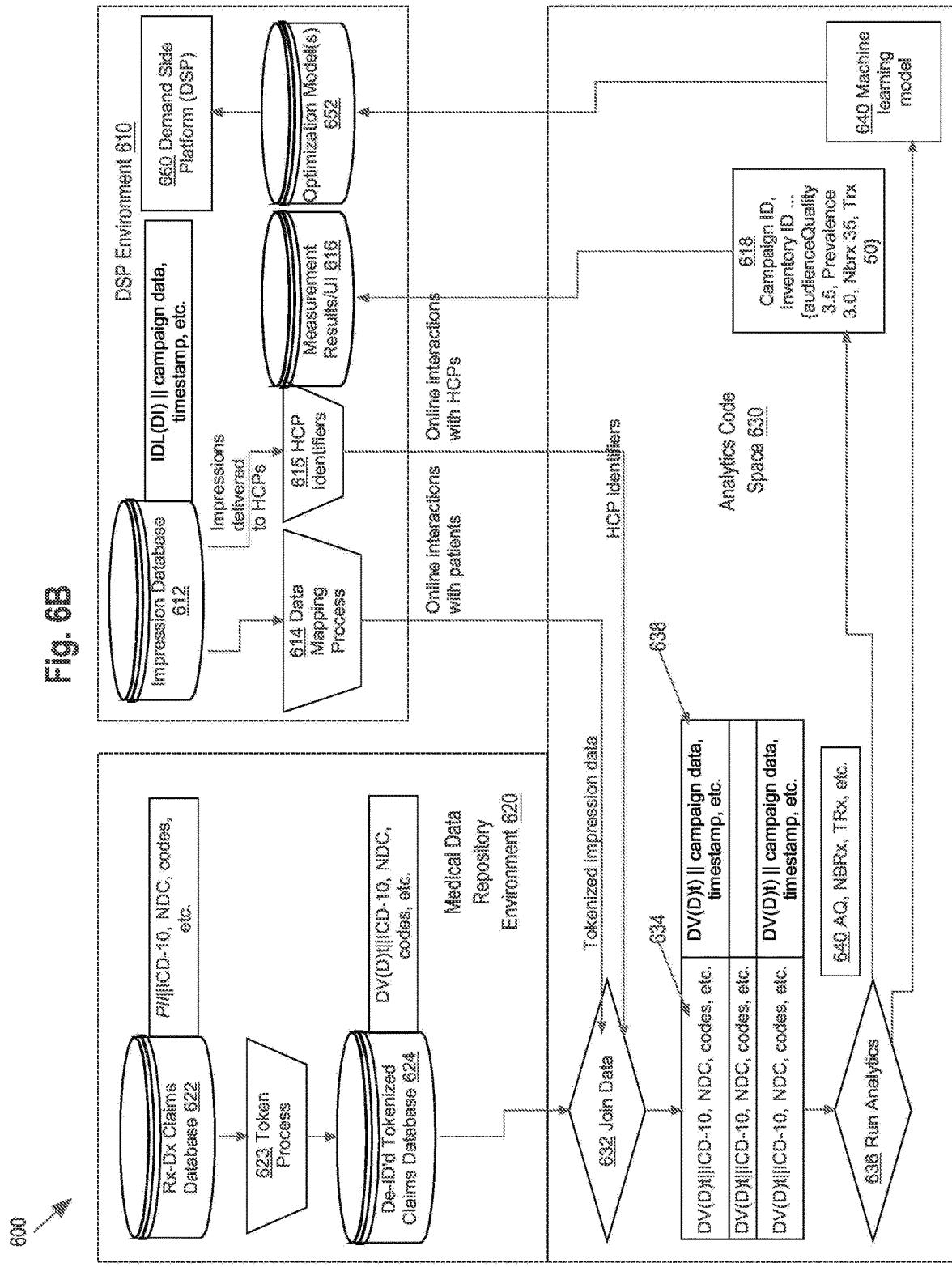
FIG. 6B illustrates the system of FIG. 6A with certain optimization elements.

FIG. 6A illustrates an example distributed computer system with which certain embodiments may be implemented. FIG. 6B illustrates the system of FIG. 6A with certain optimization elements.

In an embodiment, referring first to FIG. 6A, a distributed computer system 600 comprises a DSP environment 610, medical data repository (MDR) environment 620, and analytics code space 630. Typically, the DSP environment 610 and the medical data repository environment 620 with analytics code space 630 represent different computing domains of independent parties, but in some embodiments, they may comprise the same computing device, virtual machine instance, domain, entity, or computing center. Each of the DSP environment 610 and medical data repository (MDR) environment 620 comprises at least one computer, process, processor, or virtual machine instance, in a public or private datacenter, that is programmed to execute the functions that are further described in the following sections. Within the DSP environment 610 and medical data repository (MDR) environment 620, a computer or virtual machine instance is communicatively coupled to the other functional elements that are shown within each environment, respectively, directly or indirectly via one or more network links. Analytics code space 630 comprises a set of executable instructions that may execute on the same processors or computers that implement the medical data repository environment 620. In some embodiments, analytics code space 630 is a domain for executing custom code that may be originally authored by an entity associated with the DSP environment 610, but securely executed within the medical data repository environment 620.

In an embodiment, DSP environment 610 comprises a measurement server computer that is communicatively coupled directly or indirectly to server computer 110 and may execute using the same servers as server computer 110, or different servers. In an embodiment, DSP environment 610 comprises an impression database 612 that is programmed to store data describing impressions delivered by the DSP in advertising campaigns. In an embodiment, impression database 612 stores records 613 with column attributes such as a device identifier (DI), campaign descriptions, timestamps for parts of the campaign (e.g., times of serving various impressions, or start/end times of stages of a campaign). Each DI may be a de-identified token representing a consumer or other user of a device. In other embodiments, records 613 may use hashed emails or other identifiers associated with a consumer and/or HCP and linked to the impression data, and a DI is not required.

In an embodiment, impression data of consumers from database 612 is processed using a data mapping process 614 which is programmed to map DI values to de-identified user device tokens, which may be denoted in one example as DV(DI)t. Output from data mapping process 614, comprising tokenized impression data representing online interactions with consumers is programmatically transmitted to the join data operation 632 in analytics code space 630, which is further described in other sections herein. In database 612, from impressions delivered to HCPs, HCP identifiers 615 may be extracted and programmatically transmitted to the join data operation 632. Examples of HCP identifiers include NPIs, Medical Education (ME) numbers, or any other unique identifier of a particular healthcare provider.

In some embodiments, MDR environment 620 is owned, operated, and/or managed by an entity independent of a second entity that owns, operates, and/or manages the DSP environment 610. In an embodiment, DSP environment 610 may comprise a measurement results database 616 that is programmed to store tracked measurement results for an advertising campaign. Generating measurement result data for database 616 is described in other sections herein.

In an embodiment, MDR environment 620 may comprise a claims database 622 that is programmed to store prescription and procedure records derived or copied from medical insurance claims submissions of HCPs to insurance carriers, government agencies, or other payers. In some embodiments, claim data records include personally identifying information for patients, prescription and diagnosis (Rx and Dx) data of a large plurality of patients. As an example, this Rx and Dx data may include diagnosis (ICD-10), drug (NDC), or medical procedure (CPT) codes, or other values that describe claims for procedures, prescriptions, or other encounters of service providers and consumers. Because database 622 stores personally identifiable information (PII) in claim data records, MDR 620 will be subject to high-security techniques to prevent disclosure or unauthorized use of the data.

The MDR may implement proprietary algorithms for mapping PII to de-identified token values and computers or processes of the DSP environment 610 may access or call these algorithms via an application programming interface (API) implemented in the MDR environment. The MDR 620 also implements code to extract HCP identifiers, such as NPIs, from records in claims database 622; while these values do not require tokenization because they identify healthcare providers and do not carry the privacy implications of consumer data, they are useful in joining records in later steps to identify when the same campaign has reached the same provider and consumer and is associated with a prescription or claim for the product involved in the campaign. Data mapping process 614 may be programmed to transmit an API call to MDR environment 620, the call including a device identifier value, and to receive a response specifying a mapped de-identified token value. With this approach, in downstream steps, a given DI from data mapping process 614 can match a de-identified token value that MDR environment 620 has internally created and stored based upon PII, other available data, and proprietary algorithms executed within the MDR environment. Further, the MDR environment 620 operates to find HCP identifiers in claims data and provide them to later steps for use in record joining and matching.

In an embodiment, within the secure MDR environment 620, claims database 622 is coupled to a token process 623 that is programmed to de-identify and tokenize the claims data and store de-identified, tokenized records in a separate database 624. HCP identifiers also may be extracted from records in claims database 622 and stored in the same database 624 as for de-identified tokenized claims records but without tokenization; for example, a record in database 624 may store tokens which link consumers who were involved in a claim to such claim on a de-identified basis, but may store HCP identifiers as-is, without tokenization. Or, HCP identifiers or other attributes in records of claims database 622, whether or not they consist of conventionally recognized PII, may be tokenized or otherwise de-identified prior to storage in records in database 624. In an embodiment, records of database 624 do not include PII but are encoded with tokens for consumers which may be denoted in FIG. 6A and FIG. 6B, for example, DV(D)t. Other values in records of database 624 may be the same as in claims database 622. Data may be tokenized such that patient information associated with given codes is de-identified to comply with HIPAA and/or other legal requirements.

In analytics code space 630, de-identified tokenized claims database 624 is coupled to join data operation 632 which may be programmed to execute a join of records from database 624, output of data mapping process 614, and HCP identifiers 615. For example, data records 634 received from database 624 via join data operation 632 may be matched to records 638 that have been received from data mapping process 614 via join data operation 632 and joined based on matching values of a key such as de-identified token and HCP identifiers 615. HCP identifier 615, whether or not they consist of conventionally recognized PII, could be tokenized or otherwise de-identified prior to being joined and matched via join data operation 632 with HCP identifiers extracted from claims database 622. A result set is programmatically provided to an analytics operation 636 which is programmed to execute one or more analytics operations on the result set. The output of operation 636 is dataset 618, which specifies campaigns and metadata concerning campaigns that have reached both service provider devices and consumer devices. Analytics at operation 636 can include calculating audience quality, lift analysis, or other metrics, and the creation, training, and verification of machine learning models 640 for export to the DSP 660 as optimization models 652 for use in continuous optimization of the DSP. In an embodiment, an optimization model 652 may be the same as a machine learning model except that it has passed verification and has a logical location within the system that allows for evaluation of bid request data and use in optimization of a bidder as further described in other sections.

The output dataset 618 may be exported or otherwise transmitted to database 616 in DSP environment 610 and stored as measurement results. Within analytics code space 630, measured results also may be used to generate analytics reports, which may be used to train machine learning models 640 that can output predicted values capable of being loaded as optimization models 652 in server computer 110 to adjust parameters of a relevant advertising campaign, as further described in other sections in connection with FIG. 6B, FIG. 7C.

Figure 9:
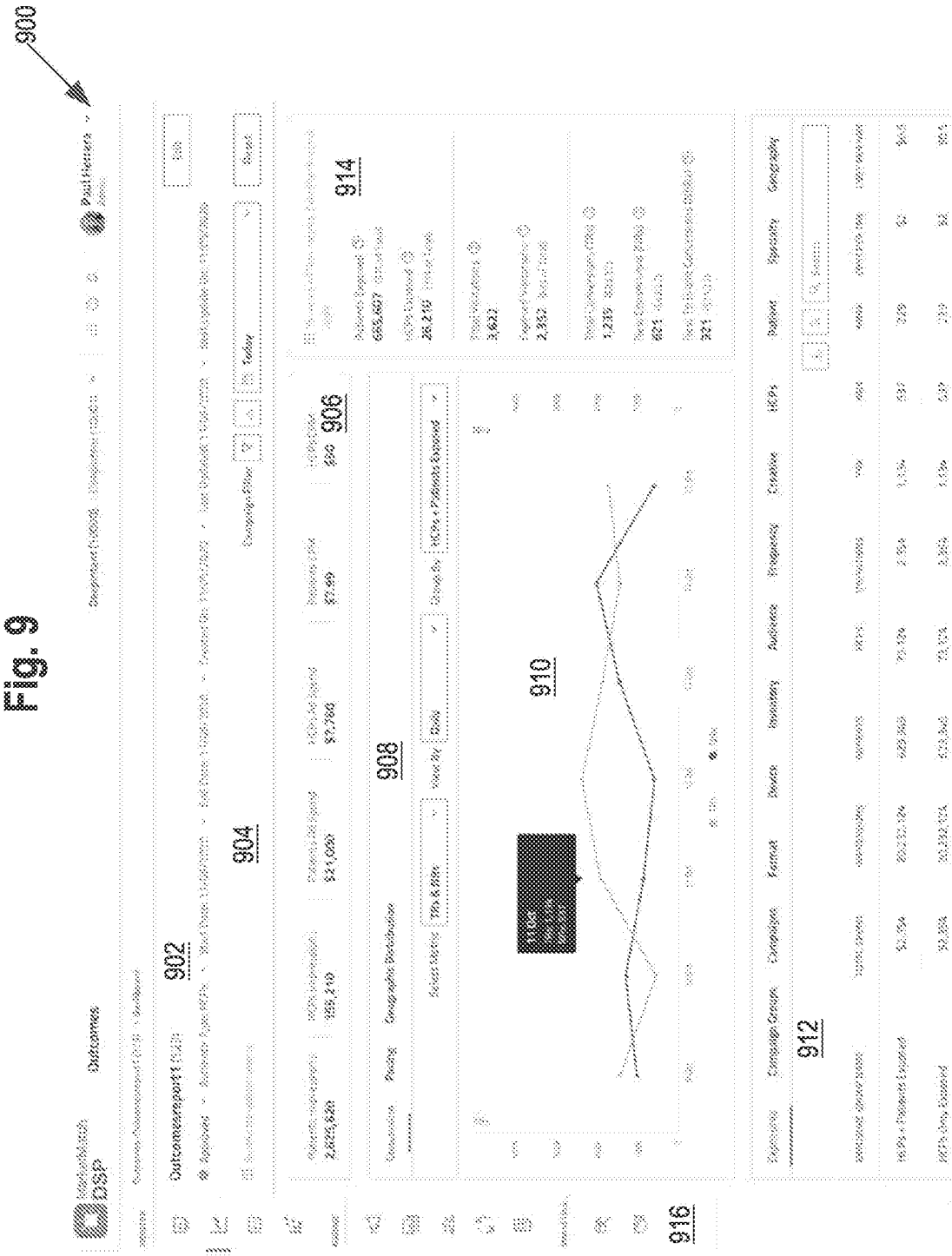
FIG. 9 illustrates an example GUI for presenting an analytics report of a measured campaign.

FIG. 7A illustrates an example measurement and management process for a given campaign. FIG. 7B illustrates an example measurement and management process for a given campaign. FIG. 7A, FIG. 7B each represent different embodiments of the following general process. A user or account sets up campaigns targeting specific healthcare provider and patient audiences, or campaigns targeting other kinds of service providers and consumers. Target audiences are defined by clinical attributes. Audiences are loaded into the DSP and attached to ad campaigns. In an embodiment, each campaign may be represented using a dataset in which one attribute specifies whether the campaign should receive integrated measurement reporting. In an embodiment, if the attribute is set so that reporting is being used, then a report is instantiated through a registration process. A new reporting job is created and will periodically refresh, update key reporting statistics, and deliver reports by merging and joining DSP data with clinical data available via the architecture described for FIG. 6. When a campaign finishes, a request to the registration API causes the system to cease to collect statistics and update the report. DSP data will be subsequently pushed to the environment on periodic update for processing. Each report consists of several dimensions of analysis ("reporting pivots"). Data will be combined with patient clinical data and HCP clinical data, and the combined dataset will run through various reporting analytic processes to update each report pivot for each report. Reports are pushed to a working database once done. Automated processes will be notified and load the data into UI database. Data is made available within a specialized graphical user interface; FIG. 9 shows one example and is further described in other sections herein. In an embodiment, the DSP may automatically optimize campaign targeting to spend more money on ads and on impressions that yield better performance, such as a lower cost per conversion or prescription.

Referring first to FIG. 7A, in an embodiment, the steps or operations of FIG. 7A may be implemented using stored program instructions of computers that implement DSP environment 610 and analytics code space 630. In an embodiment, at step 702, the process is programmed to obtain, from a DSP, impression data specifying a first set of campaigns that are associated with a first set of one or more healthcare attributes, the first set of campaigns being among a plurality of different campaigns executed by the DSP.

At step 704, the process is programmed to obtain, from the impression data, a first plurality of records with de-identified consumer tokens representing consumers who have received digital impressions of the first set of campaigns that are associated with the same first set of healthcare attributes.

At step 705, the process is programmed to obtain, from the impression data, a second plurality of records with HCP identifiers representing HCPs who have received digital impressions of the first set of campaigns that are associated with the first set of healthcare attributes.

At step 706, the process is programmed to receive, based on analytics instructions executing in a database server, a set of de-identified tokenized patient claims data records, each of the data records relating to at least one claim concerning a prescription of a specified product. These records provide a basis for matching to the records of step 704.

At step 707, the process is programmed to match the HCP identifiers in the records of step 705 to HCP identifiers in claims data records among the set of de-identified tokenized patient claims data records, each of the data records relating to at least one claim concerning a prescription of a specified product. Matching records may include some of the records that were selected at step 706. At this point, the process will have matched, in a manner that fully preserves consumer privacy, records of campaigns for which consumers received impressions; records of campaigns for which HCPs received impressions; and records of claims that involved the same patients and/or HCPs, as well as the same product involved in the campaign. These matching steps have been unavailable in prior practice. The ability to tokenize claims data in a secure environment, to tokenize impression data in the same manner, coupled with analytics such as matching tokens associated with impression records to de-identified tokenized claims records and/or with analytics such as matching HCP identifiers with impression records, optionally in combination with training a machine learning model based on analytics output to predict bids or other DSP parameters that may be automatically updated or modified in the DSP, represents a key advance in the art that the inventors conceived in an inventive moment. It enables extracting new meaning from data using computer executed operations that have not previously been used in the combination presented in this disclosure.

At step 708, the process is programmed to receive, from the database server, a result set of one or more integrated measurement records specifying one or more measured campaigns among the plurality of different campaigns, the one or more measured campaigns being associated with the prescription of the specified product in at least one claims data record that is associated with at least one of the consumer tokens and/or at least one of the HCP identifiers.

At step 710, the process is programmed to generate and cause presenting one or more analytics reports based on the integrated measurement records. Particular embodiments may repeat one or more steps of the method of FIG. 7A, where appropriate.

As one particular example of this overall process, two advertising campaigns (one for HCPs and one for patients) may be linked and registered with the MDR environment 620. These campaigns may be marketed to deliver ads about a new medication to patients with a particular health condition (for example, COPD) and HCPs who specialize in treating patients with this particular health condition (COPD). Impression data of the advertising campaign for patients may be pushed to the MDR environment, where analytics instructions may be executed to extract de-identified tokens of patients having a diagnosis code indicating that they have COPD, or having drug codes/NDCs indicating that they take medications for COPD. By contrast, because HCP information does not need to be anonymized, HCPs associated with the condition of COPD may be directly identified at the measurement server computer 610 or DSP system 110 by NPIs or other identifiers. As an example, NPIs of targeted HCPs may be identified by identifying their practice/specialty area, or by prescriptions/drug codes written by that NPI for COPD medications. Thus, impressions data of the advertising campaign for HCPs may be pushed directly to the MDR environment 620 with all information already determined. As an example, the server computer 110 has already determined which NPIs have been served the targeted advertisements.

With these HCP and patient campaigns now linked, effects of the two campaigns may be determined with respect to changing patient/HCP behavior. As an example, the MDR environment may observe an increase in the number of prescriptions associated with the NDC code for the new advertised medication. In particular embodiments, this number may be measured at very detailed levels. For example, the increased number of prescriptions/script-writing behavior for the new advertised medication may be determined and shown for when an impression was shown only to a patient, only to an HCP, to both a patient and an HCP, or to either or both a patient and HCP at a time close to when a particular encounter between these two parties occurred, as indicated in records of claims database 622.

In particular embodiments, this measurement may be updated at regular intervals, such as weekly. In this situation, consumer data at the MDR environment 620 may be refreshed (for example, new prescriptions having the desired NDC code, new visitation codes indicating qualified encounters between targeted patients and HCPs, or new patient records having a diagnosis code indicating COPD diagnosis may be determined). Coverage of the ad may also be determined; as an example, it may be determined that an ad had 62% coverage, meaning that the ad was served to either the patient or the HCP in 62% of the total recorded visitations. Similarly, at the DSP environment 610, impression data for the advertising campaigns may be refreshed (for example, records of NPIs that have received the COPD ad, number of ads displayed on various websites, and the total amount of spending per impression may be determined). This data may be pushed to the analytics code space 630 of MDR environment 620, where it may be joined with the de-identified consumer data via operation 632. This data may then be matched to refreshed data of the MDR environment 620, such as the number of prescriptions written for the NDC code over the past week.

In an embodiment, data concerning the performance of the advertising campaign may then be fed into a machine learning algorithm, which determines how best to optimize and update parameters of the advertising campaign. Referring now to FIG. 6B, in an embodiment, analytics operation 636 may be coupled to a machine learning model builder comprising an executable script that trains a machine learning model 640 against all available data in the analytics output of analytics code space 630. User data, bid request data, and results of analytics operation 636 all may contribute to the machine learning model builder and its output in the form of a resulting machine learning model 640, which may be constructed initially within analytics code space 630 and exported to DSP environment 610 as part of optimization models 652.

In an embodiment, optimization models 652 are programmed to automatically modify one or more parameters of a campaign in the DSP 660 based on results that have been derived via analytics operation 636 from real-world clinical data and campaigns. The automated modification of campaign parameters may result in more efficient media investments in the form of higher return on advertising spend (ROAS) or lower cost per conversion, such as prescriptions or procedures. For example, optimization models 652 may be programmed using machine learning classifiers coupled to programmed optimization functions to receive, as input, bid request data of existing campaigns in DSP 660 and demographic segment data associated with campaigns that were identified as successful in analytics operation 636, and to output parameter values for bids and/or segments. For example, output of models 652 may drive pricing or fulfillment of ad requests that are configured in DSP 660.

Optimization models 652 may interoperate with UI 616 to present a graphical user interface that is programmed to receive optimization input, such as user input specifying an optimization goals. Examples of goals include optimization based on cost per total prescriptions, cost per new prescription, cost per new-to-brand prescriptions, or cost per action (CPA).

As an example, the change over the past week in the number of prescriptions with the desired NDC code may be compared against various parameters, such as format, publisher/website, specialty, geography, frequency, etc. As an example, if it is determined that impressions from a first website led to a relatively large number of prescriptions being written for the new COPD drug, while impressions shown on a second website resulted in only a relatively small number of new prescriptions being written, spending may be automatically shifted to decrease the number of impressions spent on the second website, while increasing the number of impressions purchased on the first website. Similarly, if it is determined that impressions shown in a particular geographical area led to more scripts being written for the new COPD drug, then the DSP system may refine the targeting parameters of the advertising campaign to focus on presenting impressions to patients/HCPs in that geographical location, even if they are presented on the same websites. Thus, the data used for targeting ads in the first place is the same data used to measure the performance of the campaign, thus enabling greater accuracy and optimization in reaching the desired patients/HCPs and the influence of the campaign itself.

Figure 7C:
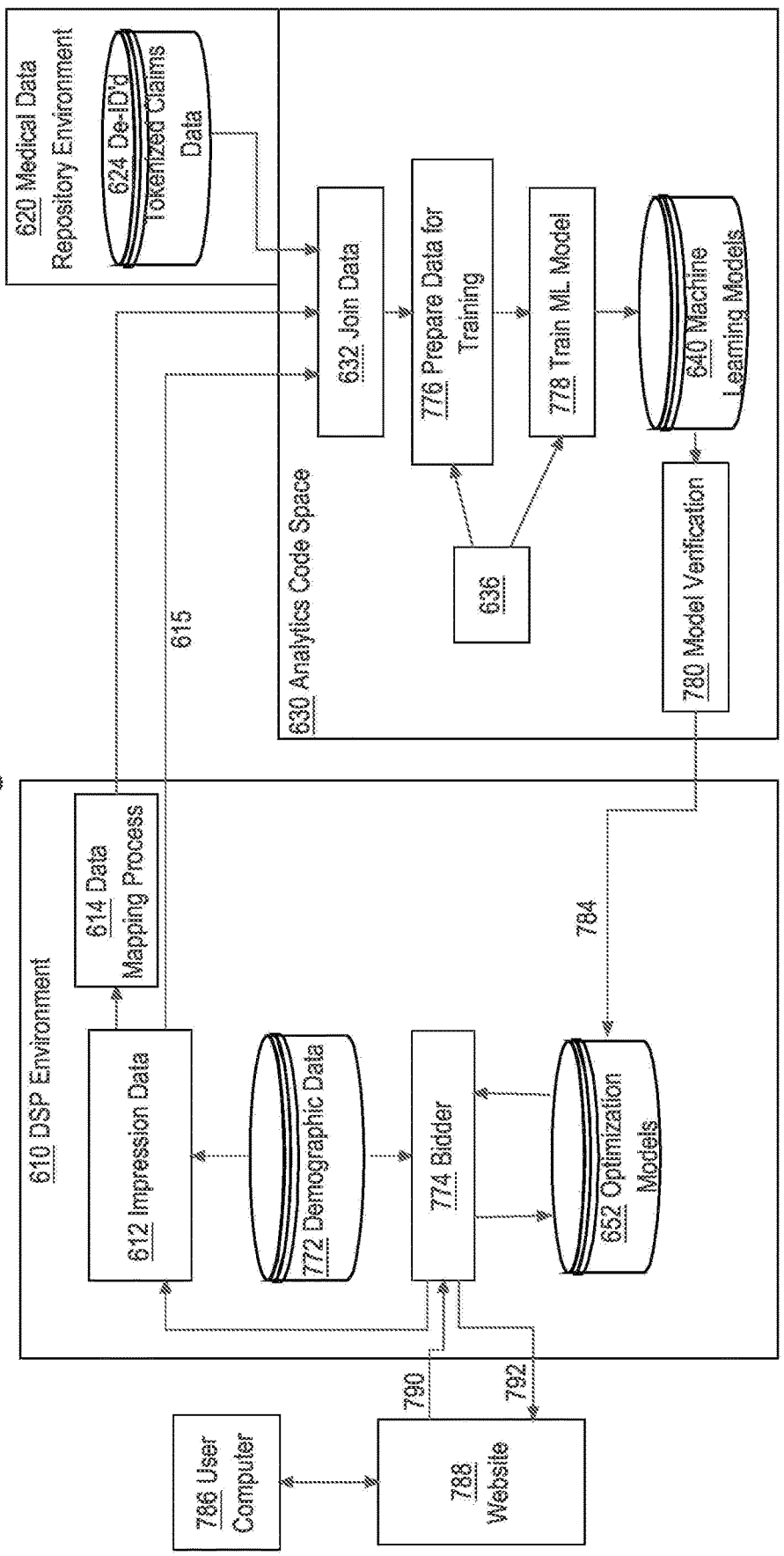
FIG. 7C illustrates example functional elements and data flows in an embodiment of DSP optimization.

FIG. 7C illustrates example functional elements and data flows in an embodiment of DSP optimization.

In an embodiment, within DSP environment 610, impression data 612 for impressions related to campaigns is processed via data mapping operation 614 and delivered with HCP identifiers 615 to join operation 632 within the analytics code space 630. For example, an impressions log file may be transferred to analytics code space 630 for secure processing within that environment. In some embodiments, demographic data 772 also is transferred from DSP environment 610 to analytics code space 630 in combination with impression data 612, and comprises records describing demographic characteristics of audience segments and/or consumers who are represented in the impression data 612. Demographic data 772 also may comprise values for publisher website, time of day the ad is served, or device type.

In some embodiments, the impressions data 612 and demographic data 772 may be tokenized, before transfer, using commercially available de-identified tokenization software. The transfer of data from DSP environment 610 to medical data repository 630 also may include selecting specified fields that are necessary for model training.

In one embodiment, impressions data 612 and demographic data 772 as combined and transferred to join data 632 comprises a plurality of records each having values or attributes for:
Type of inventory ("site", "app")
Type of device ("phone", "personal computer", "tablet")
Endemic publisher or non-endemic ("true" or "false")
Type of creative ("banner" or "video")
Demographic segments (array of demographic segments for a given impression. A sequence of segment values as "<segment ID>:1" s)
GEO state
Inventory ID
ZIP3 (3-digit zip code).

Within the analytics code space 630, impressions data 612 and the demographic data 772 are joined to de-identified, tokenized claims data 624, as indicated by join data operation 632. In an embodiment, de-identified tokens and/or HCP identifiers are used as common key(s) in the join operation. The join operation 632 may result in creating and storing a result file.

In an embodiment, at operation 776, the result file is prepared for training. At operation 778, a machine learning model 640 is trained using the result file as a training dataset. In some embodiments, operations 776, 778 form part of the run analytics operation 636 of FIG. 6A, FIG. 6B.

At operation 780, the trained machine learning model 640 is subjected to a verification process, which may be programmed to verify that the trained model complies with data privacy or de-identification requirements. For example, verification may address whether the trained model complies with HIPAA when patients or healthcare data are involved.

When verification is successful, the trained machine learning model 640 is exported or transferred to DSP environment 610, as represented by optimization models 652, and path 784 of FIG. 7C. In an environment, DSP environment 610 comprises a bidder 774, implemented as a functional element in software and programmed to execute in the manner further described in this section and other sections. A bidder 774 may load the optimization model(s) 652 and evaluate bid request data 790 using the trained models to result in outputting predictions of bid values or other parameters of the bidder 774 that can be used to modify operation of the DSP in relation to the campaign. For example, assume that user computer 786 of a consumer or service provider contacts a website 788 or other device by which digital advertisements are placed. In the course of serving digital ads to website 788, which delivers bid request data 790 to the bidder 774. Bid request data 790 may be enriched with demographic data 772 and supplied to optimization model(s) 652 for use in an evaluation or execution of the model to produce classification or prediction output, for example, to predict the likelihood of a conversion, such as the likelihood of a consumer being prescribed a treatment or product, and/or the likelihood of a service provider prescribing a treatment or product. Thus, after having imported the optimization model 652, bidder 774 uses the optimization models 652 and scores incoming bid request data 790 using Open Real-Time Bidding (OpenRTB fields) as well as demographic data 772. Based on the predictions of the optimization model 652, the bidder 774 may adjust bid price accordingly, to target more relevant advertisements served on path 792 to user computer 786 of consumers and/or service providers and optimize towards improved conversions or other goals.

Output predictions from optimization models 652 may be automatically loaded to bidder 774, or an administrative user accessing the DSP environment 610 may conduct review through a user interface and apply configuration changes bidder 774 manually.

In some embodiments, execution of optimization models 652 in relation to bidding data, output of predictions, and configuration of the DSP based on the predictions may be fully automated using programmatic control. Using this approach, or the approach described above, embodiments may execute continuous optimization on the performance of the bidder 774 via a feedback loop in which execution of optimization models 652 on newly received impression data 612 causes rapid updates to bids or other parameters of the bidder 774 for serving advertisements to user computer 786 via path 792 to improve conformance to goals. Thus, the process of optimization includes the bidder being optimized by the optimized model which reads the bid request data and demographic data and causes the bidder to determine on whether to bid and how much to bid, and using the output to cause serving an advertisement based on those optimized parameters.

In one specific implementation, the machine learning model 640 that is trained at operation 778 to eventually result in optimization models 652 may implement a gradient boosted decision tree; other embodiments may use deep learning neural networks or other forms of machine learning models. For example, in some embodiments the XGBoost library may be used to implement the model. For this implementation, preparing data at operation 776 may comprise converting the result data into a format suitable for the XGBoost library. In one approach, each record has a label assigned that specifies whether the record is converted or not, based on the existence or a miss of a medical record or transaction. A binary value may be used. Further, all other data points are represented as integers.

In one specific implementation, operation 776 may comprise converting the training dataset into LibSVM format, which may be expressed as label feature1:1 feature2:1. The value label:1|0 is a Boolean flag that demonstrates if a match was found between a medical transaction record and a given impression record and can have the value ("1") for found or ("0") for not found. LibSVM is just one of the formats supported by the XGBoost library, and other embodiments may use other formats to submit test datasets.

Further, in one implementation, all features are hashed using the murmur3 hashing algorithm, after which a modulus operation is executed to reduce the number further. The hash operation may be expressed as murmur3('f01:<value>'), where f01 is an index of the feature and <value> is a value of the feature. As an example, for the InventoryType="site", the feature may be "166685:1", where 166685 is a murmur3 hash of "f01:site". The "murmur3" algorithm is only one example of a hash algorithm that may be used, and other embodiments may use different hash algorithms.

As an example of a suitable machine learning model, XGBoost is a decision-tree-based ensemble algorithm that uses a gradient boosting framework. In prediction problems involving structured data or tabular data, algorithms based on decision trees are preferred. Other decision tree models or other machine learning models may be substituted in other embodiments. In one embodiment, the XGBoost library may be configured with the following parameters:

eta—Step size shrinkage used in update to prevent overfitting max_depth—Maximum depth of a tree num_round—The number of rounds for boosting min_child_weight—Minimum sum of instance weight (hessian) needed in a child gamma—Minimum loss reduction required to make a further partition on a leaf node of the tree objective—Specify the learning task and the corresponding learning objective tree_method—The tree construction algorithm used in XGBoost. XGBoost supports approx, hist and gpu_hist for distributed training. Experimental support for external memory is available for approx and gpu_hist.

eval_metric—Evaluation metrics for validation data, a default metric will be assigned according to objective (rmse for regression, and logloss for classification, mean average precision for ranking)

A detailed explanation of these parameters is set forth in the file "parameter.html" in the path "/en/latest/" of the domain xgboost.readthedocs.io. Parameter values may be tuned after observing training results or evaluation results, thereby providing a process of continuous optimization of the DSP 660.

FIG. 7B illustrates an example measurement and management process for a given campaign.

Assume for purposes of illustrating a clear example that a computer, account, or user represented by element 732 interoperates with a planner 734 of the DSP system 110 to define a campaign directed to HCPs and defining an HCP audience. Asynchronously, an operational or Ops function 736 of the DSP is used to create a consumer campaign directed to patients. Definition of the consumer campaign may involve interoperating with a patient modeling environment 740 to define a consumer audience. Data representing both the service provider audience and consumer audience is loaded in DSP 110. Campaign setup processes may execute, for example, using the audience modeling and other techniques discussed above with respect to FIG. 1, FIG. 2, FIG. 3, FIG. 4, FIG. 5.

At block 742, in one embodiment, the process executes a test to determine whether the advertising campaign has enabled an integrated monitoring and reporting function through the DSP system 110. If the function has not been enabled, then DSP system 110 executes in the manner described above and integrated reporting does not execute. If block 742 is TRUE or YES, then control transfers to block 744.

At block 744, the process is programmed to test whether the campaign is new. "New," in this context, means that data for the campaign has not been posted or registered with the MDR 620. If block 744 is TRUE or YES, then control transfers to block 746 and the new campaign may be registered with the MDR environment 620. Registration, in one embodiment, comprises executing an operation to transfer, to MDR environment 620, a dataset 748 comprising data describing a campaign. For example, a POST operation may be used to transfer data in the form of a JSON blob, parameterized HTTP, or other structured data transfer with a dataset 748. In an embodiment, dataset 748 specifies an organization, advertiser, one or more HCP campaign groups, one or more target numbers of HCPs, one or more patient campaign groups, one or more patient target attributes, and one or more identifiers of metrics for measurement. Custom code executing in analytics code space 630 may be programmed to execute, in response to a registration operation, transmitting to a configuration database 751, a definition of a report or other output.

If the test of block 744 is FALSE or NO, then in an embodiment, control transfers to block 750 at which the process is programmed to determines whether an analytics report on the performance of the advertising campaign should be updated. Block 750 may represent inspecting a stored schedule and testing whether a system clock value returns a date-time value that is equal to a scheduled report execution date. As an example, the DSP measurement server 610 may automatically execute a first iteration of running, measuring, and updating an advertising campaign based upon a digitally stored execution schedule. Such an execution schedule may result in the report being generated upon request or at regular intervals, such as weekly, daily, or in real time. Or, the test of block 750 may represent a CRON job or other scheduled job that executes according to a schedule and triggers a signal to MDR environment 620 at a specified time.

If the test of block 750 is FALSE or NO, then monitoring of the advertising campaign may continue. If the test of block 750 is TRUE or YES, then in an embodiment, operations 632, 636 (FIG. 6) may execute, in which tokenized impression data and HCP identifiers may be sent to the MDR environment 620 to be joined with tokenized claims data records with HCP identifiers from database 624. In some embodiments, metadata concerning impressions also is transmitted and used in the join operation. In an embodiment, as indicated at block 752, 753, reports of campaign impression data resulting from actual impressions to service providers and/or consumers may be generated and transmitted or posted to the MDR environment 620. For example, for one or more of the measured output campaigns, a set of impressions data of a first impression associated with a particular campaign among the plurality of different campaigns may be updated to generate an updated first impression. A set of de-identified patient tokens representing consumers associated with the first set of one or more healthcare attributes may be appended to the updated first impression, and the particular campaign may be updated based on the updated first impression and the appended set of the de-identified consumer tokens. Subsequently, one or more second iterations of running, measuring, and updating the advertising campaign based upon a digitally stored execution schedule may be executed using newly received campaign impression data from the impression database 612. In particular embodiments, the set of impressions data may be updated, and the updated first impression may be generated, by a machine-learning algorithm such as one performed by an artificial neural network, such as that described below with respect to FIG. 10. As detailed at block 752, an update process may be programmed to fetch campaign impression data, for example from a scratchpad database 756, to combine the campaign impression data with tokenized, de-identified clinical/patient data, execute reporting/analytic routines, and transmit or push updated reports to the scratchpad database 756 as further represented in block 754.

In an embodiment, at block 758, reporting data is processed for presentation and loaded to a user interface (UI) database 760 for storage. At block 762, the stored analytics reports may be retrieved and presented via a user interface.

In particular embodiments, the measurement server computer may obtain, from a demand-side platform (DSP), impression data specifying a first plurality of de-identified consumer tokens representing consumers who have received digital impressions of a first set of campaigns that are associated with a first set of one or more healthcare attributes, the first set of campaigns being among a plurality of different campaigns executed by the DSP. Each de-identified consumer token may be linked to a first healthcare attribute of the first set of healthcare attributes and may be further linked to a first de-identified tokenized claims data record from among a set of de-identified tokenized claims data records. Further, each campaign in the first set of campaigns may be defined in the DSP using at least one clinical attribute in the first set of healthcare attributes. As examples, each clinical attribute may be any of an ICD-10 code, CPC code, or NDC code.

In particular embodiments, the measurement server computer may obtain, from the DSP, impression data specifying a second plurality of healthcare provider (HCP) identifiers representing HCPs who have received digital impressions of the first set of campaigns that are associated with the first set of healthcare attributes. As an example, the HCP identifiers may be National Practitioner Identifier (NPI) values.

In particular embodiments, the measurement server computer may receive, based on analytics instructions executing in a database server, a set of de-identified tokenized claims data records, each of the data records relating to at least one claim concerning a prescription of a specified product.

Figure 8:
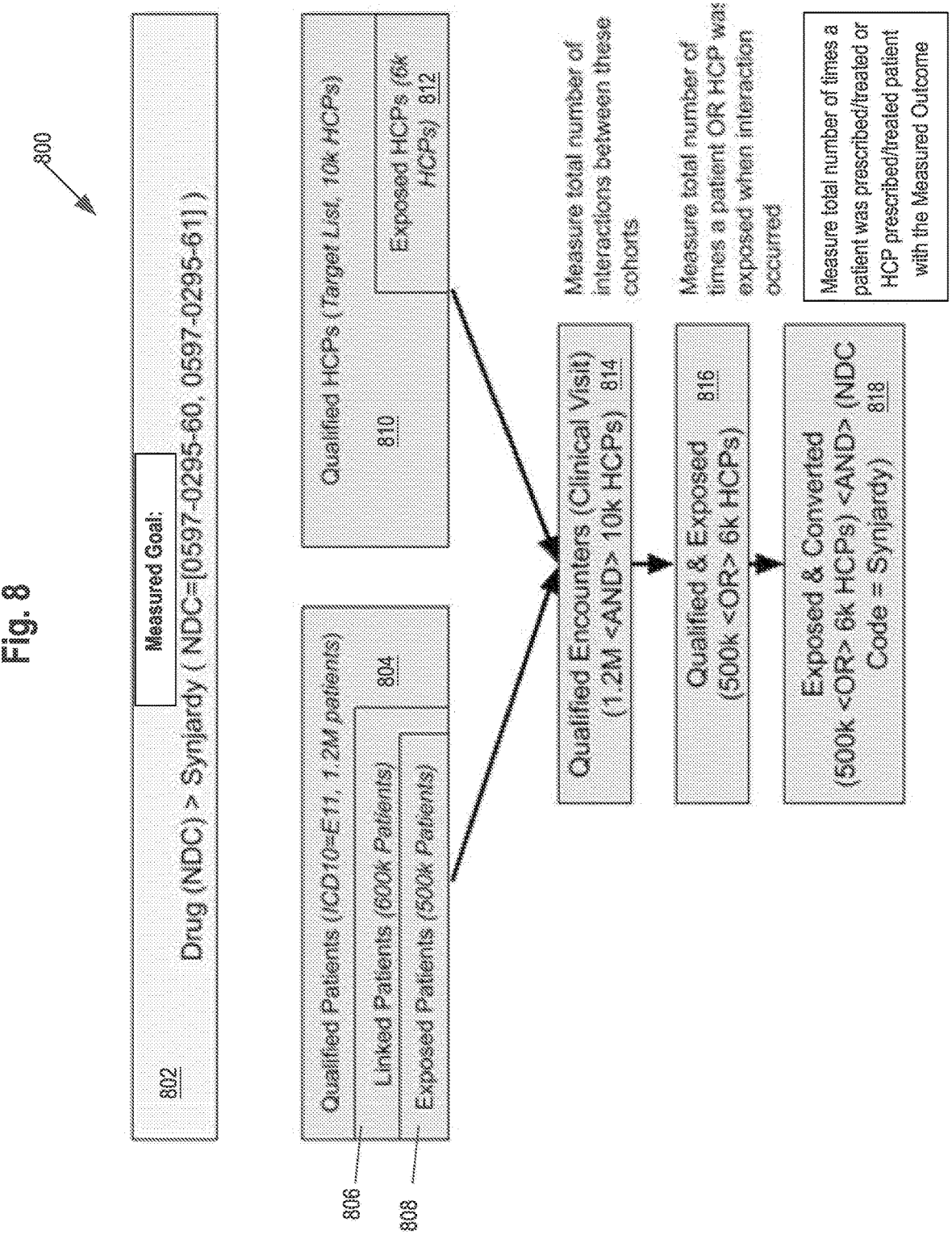
FIG. 8 illustrates an example data flow in for a given campaign.

Using the foregoing approach, large datasets may be successively refined into smaller datasets representing the service providers and/or consumers who are qualified for a campaign, exposed to a campaign, and resulted in a conversion. FIG. 8 illustrates an example report setup process for a given campaign in which successive filtering and flow-down of audiences occurs, resulting in actionable result measurements.

In an embodiment, the campaign definition and audience definition processes described above for FIG. 7B may result initially in creating a measured goal value 802 for a campaign, a first dataset of qualified patients 804 and a second dataset of qualified HCPs 810. In an embodiment, the measured result may specify a particular drug in terms of one or more NDC values that identify the drug for national regulation or claims purposes. In the example of FIG. 8, measured goal 802 specifies SYNJARDY, which is identified by NDC values of 0597-0295-60 and 0597-0295-61. Further, in the example of FIG. 8, qualified patients 804 may comprise patients who have been identified in a diagnostic encounter in which an HCP coded a claim using ICD10 value "E11"; in one test execution, this code yielded a set of 1.2 million patients. Qualified HCPs 810 typically derives from a target list from privately prepared or proprietary sources and might comprise 10,000 HCP identifiers or more.

The qualified patients dataset 804 may be filtered a first time to a number of linked patients 806, meaning patients that are qualified and that are further associated with a particular token, linked to data from the database server 620. The linked patients 806 may be filtered again to identify exposed patients 808, meaning patients who are known to have been exposed to an ad as indicated by exposure data from the DSP. In this example, about 500,000 identifiers are in the exposed patients dataset 808.

The qualified HCPs dataset 810 may be filtered to yield exposed HCPs 812, numbering about 6,000.

Additionally, or alternatively, data from the first set of campaigns may be obtained. As an example, this data may include a number of qualified HCPs (HCPs having targeted NPIs, as determined by their claims data, prescription data, demographic data, practice/specialty data, or other relevant data as discussed with respect to FIG. 1) and a number of exposed HCPs (HCPs exposed to an ad).

As shown next, via the data join operations that have been previously described, a qualified encounters dataset 814 may be formed to measure the total number of interactions between the qualified patients 804 and qualified HCPs 810, resulting in creating and storing a Qualified Encounters dataset 814. In the example of FIG. 8, dataset 814 will have some number less than the 10,000 HCPs representing all HCPs and patients who interacted in the same clinical visit.

The resulting dataset may be transformed again to capture a qualified and exposed count value 816, indicating a total number of times that either a qualified patient or a qualified HCP was exposed to the campaign associated with measurement goal 802 near the time when an interaction occurred.

Finally, an Exposed and Converted count value 818 may be formed, indicating a total number of times that patients were prescribed or treated with the product associated with the measured goal, or that the HCP or service provider wrote a prescription or performed a treatment. In the example of FIG. 8, value 818 comprises the set of qualified and exposed records that also are coded with one of the NDC codes for SYNJARDY or whatever other item is identified in the measured goal 802.

In particular embodiments, the measurement server computer may receive, from the database server, a result set of one or more integrated measurement records specifying one or more measured campaigns among the plurality of different campaigns, the one or more measured campaigns being associated with the prescription of the specified product in at least one claims data record that is associated with at least one of the consumer tokens and/or at least one of the HCP identifiers.

In particular embodiments, the measurement server computer may generate and cause presenting one or more analytics reports based on the integrated measurement records. In particular embodiments, the result set may be generated based on the analytics instructions executing, at the database server/MDR environment 620, one or more database join operations on the claims data records, consumer tokens, impression metadata, and HCP identifiers. As an example, this generating and causing presenting of the one or more analytics reports may include measuring a total number of interactions between consumer tokens and HCP identifiers in qualified encounters. As another example, this generating and causing presenting of the one or more analytics reports may include measuring a total number of interactions between consumer tokens and HCP identifiers in qualified encounters when a particular consumer token or a particular HCP identifier was exposed to a particular campaign among the plurality of different campaigns. As yet another example, the generating and causing presenting of the one or more analytics reports may include measuring a total number of interactions between consumer tokens and HCP identifiers when a particular consumer token or a particular HCP identifier was exposed to a particular campaign among the plurality of different campaigns and a particular product in the particular campaign is specified in a claims data record concerning the particular consumer token.

As yet another example, the generating and causing presenting of the one or more analytics reports may include generating a data value indicating an elapsed time between a timestamp of a first digital impression associated with a particular campaign among the plurality of different campaigns and a first measured campaign of the particular campaign. This value may enable the organizer of the advertising campaign to determine the effect and importance of different frequency levels of ads served to HCPs and patients prior to being treated with the targeted treatment. Presenting this elapsed time from the first impression to first measured goal may further enable the organizer to understand what sort of frequency is needed to influence results.

FIG. 9 illustrates an example GUI display for presenting an analytics report of a measured campaign.

In one embodiment, a GUI 900 comprises a status panel 902, a filter panel 904, a summary panel 906, a graph panel 908 comprising a graph 910, an analytics table 912, a funneled data panel 914, and a toolbar 916. In an embodiment, status panel 902 is programmed to display one or more metadata values relating to other aspects of the GUI 900, such as approval status, audience type, start date, end date, date of creation or updating, and/or other metadata. Example values appear in status panel 902 of FIG. 9.

In an embodiment, filter panel 904 comprises GUI widgets that are programmed to receive selections of filter criteria for data represented in elements 908, 910, 912 and to apply specified filter criteria to the data. In the example of FIG. 9, a campaign filter specifying TODAY has been selected, and in response, the system is programmed to filter data for the current date only and present the filtered data in other elements of GUI 900. In an embodiment, the summary panel 906 comprises count values specifying total impressions to consumers, total impressions to HCPs, spending values and cost values. In an embodiment, the run analytics element 636 of FIG. 6A, FIG. 6B is programmed to execute calculations within the analytics code space 630 to generate foundation data for the elements of FIG. 9.

In an embodiment, a graph panel 908 comprises one or more GUI widgets which, when selected, are programmed to cause generating or updating the graph 910. In the example of FIG. 9, GUI widgets specify TRx and NRx as a metric, a Daily view, and grouping by HCPs+Patients Exposed. Graph 910 reflects these parameters. In an embodiment, selecting different GUI widget options causes recalculating and updating graph 910.

In an embodiment, analytics table 912 comprises a plurality of selectable tabs, which are labeled "Exposures," "Campaign Groups," and with other labels in the present example. Labels are programmed as executable links which when selected cause displaying different data in the table 912. In the example of FIG. 9, the Exposures label is selected and table 912 comprises rows specifying exposure groups and analytics data relating to those groups. The funneled data panel 914 may be programmed to display successively narrower or smaller counts of individuals, accounts, or records based on different analytical criteria or calculations such as exposure counts, visitation counts, and conversion counts. The toolbar 916 may be programmed to display a plurality of different selectable display tools which when selected cause the system to execute functions such as changing the type of graph (line, bar, scatter plot, etc.), applying display zoom functions, or others.

Based on programmed analytics calculations executed using the functional elements described previously, data in GUI 900 may aggregate patient and provider script-writing behavior data at various dimensions (creative, publisher, format, audience, etc.), thus enabling buyers running advertising campaigns to visualize the benefit and performance of various ad serving dimensions and make further optimizations. The data reported in GUI 900 also may be used as a training dataset to train one or more machine learning models to predict bids or other values for updating one or more elements of DSP 660, such as bidder 774 (FIG. 7C), to automate campaign optimization. One example benefit of campaign optimization is making campaigns more effective by reducing ad spend on publishers and geographies that do not have large numbers of performing patients.

Panels of GUI 900 may be programmed to display reporting dimensions and analytics as scorecards. As an example, the variables discussed above and/or any of the following analytics may be shown:

HCPs Impressions: The number of impressions delivered to HCP campaigns linked to the measurement report.

HCPs Exposed (and % Reached): The number of HCPs reached with an ad (from NPI Level Reporting) and the % of HCPs reached from the original target list (% Reached).

HCPs Ad Spend: The total cost of ads delivered to HCP campaigns linked to the measurement report.

CPM—HCP: The unit cost of ads delivered to HCP campaigns linked to the measurement report.

Patients Impressions: Total impressions delivered to patient campaigns linked to the measurement report.

Patients Exposed (and % Reached, and % Linked): Number of patients exposed to an ad (linked to data from the database server).

Patients Ad Spend: Total cost of impressions delivered to patient campaigns linked to the measurement report.

CPM—Patient: The unit cost of ads delivered to patients.

In these analytics, "Total Patients" may be defined as the number of unique patients, as represented by the de-identified consumer tokens, that are "qualified" or "selected" as having a target ICD-10, CPT, or NDC code. In particular embodiments, this value may be calculated via Boolean logic as provided during campaign setup as "TARGET_ATTRIBUTES". This value may further be used to calculate the "% population" metric. Similarly, "Linked Patients" may be defined as the number of patients that are qualified and that are further associated with a particular token, linked to data from the database server. This value may be further used to calculate a "% Linked" metric. In particular embodiments, if the ad serving company only wishes to measure a patient campaign, HCPs for qualified HCPs may be used in further calculations, but the "HCP Exposed" would be set to 0.

Panels may be programmed to display reporting measures for each analytics report including any of:

Total Spend: Sum of ad spend from the DSP for impressions purchased.

Impressions: Sum of impressions from the DSP.

Visitations: Cases when qualified patients and qualified HCPs were observed as interacting within the claims data (for example, type 2 diabetes patient and targeted HCP generated a claim).

Total Prescribed (TRx): Total prescriptions written by HCPs for a particular drug over a specific period of time. This value may include prescriptions for refills and renewals (scripts patients get when they run out of refills). In contrast, the NRx value below may not include refills but may include renewals.

Newly Prescribed (NRx): Count of new prescriptions issues. NRx may not include refills but may include renewals. NRx may differ from the NBRx value below in that the NRx metric may not consider whether or not the patient has previously used the product.

New-to-Brand Prescribed (NBRx): Count of patients starting a prescription drug who have not previously used the product.

Cost Per TRx: Sum of the advertising spend (from the DSP) spent for the impressions divided by TRx.

Cost Per NRx: Sum of the advertising spend (from the DSP) spent for the impressions divided by NRx.

Cost Per NBRx: Sum of the advertising spend (from the DSP) spent for the impressions divided by NBRx.

Total Visitations: The number of times when a patient (from Total Patients) and a targeted HCP appeared together in a claims data record from the database server 620 (indicating that there was a visit or some sort of opportunity to be prescribed with a drug). In some embodiments, "Total Visitations" may be programmed as the number of times when a clinically relevant consumer and a targeted service provider appeared together in a claims data record, and/or the number of times when a targeted clinically relevant consumer and a clinically relevant service provider appeared together in a claims data record.

Exposed Visitations: The number of times when visitation happened and either the HCP or the patient was exposed to an ad before the timestamp of the visitation.

Total Conversions: The total number of conversion events (from Measured Results) linked to users targeted with an ad, as well as the total cost of these conversions (sum of ad spend for all users divided by the TRx volume).

New Conversions: The total number of new conversion events (from Measured Results) linked to users targeted with an ad, as well as the total cost of these conversions (sum of ad spend for all users divided by the NRx volume).

New-to-Brand Conversions: The total number of new to brand conversion events (from Measured Results) linked to users targeted with an ad, as well as the total cost of these conversions (sum of ad spending for all users divided by the NRx volume).

Reporting tables may display any of the following analytics:

Exposures: A report that illustrates the relative effectiveness of the ads by HCP and Patient exposure groups. This report may include any of the following analytics:

HCP+Patient Exposed: Visitations when both a qualified/targeted HCP was exposed with an ad and a qualified patient was exposed with an ad.

Patient Only Exposed: Visitations when only a qualified patient was exposed

HCP Only Exposed: Visitations when only a qualified HCP was exposed.

No Exposure: Visitations when no qualified HCP and no qualified patient was exposed.

Campaign: A report that illustrates the performance of different campaigns and the users exposed to ads from these campaigns.

Format: A report that illustrates the relative performance of different inventory formats sourced from inventoryType (Banner, Video, CTV, Audio, Native, etc.).

Device: A report that illustrates the relative performance of different device impressions sourced from bidRequest.device.type.

Inventory: A report that illustrates the relative performance of different types of publisher inventory (endemic vs non-Endemic), individual publishers, etc.

Audience: A report that illustrates the relative performance of users within different audiences (such as one report for patients, and another for HCPs). In particular embodiments, this report may be sourced from dataCharges in impressions.

Frequency: A report that gives guidance as to the importance of different frequency levels of ads served to HCPs and patients prior to being treated with the targeted treatment.

Here, the elapsed time from the first impression to first measured result may be shown to help buyers to understand what sort of frequency is needed to influence results in various audiences (such as patient audiences vs HCP audiences).

Creative: A report that gives guidance as to the relative performance of different creatives to drive results.

Physician: A report that illustrates individual physician-level results/behaviors. This may be similar to NPI reporting but may more specifically show results at an individual physician level.

Specialty: A report that illustrates the performance of different specialties when an HCP campaign is active.

Patient: A report that illustrates the performance of different model thresholds as well as different demographic segments.

Geography: A report that illustrates the performance of each state as well as each DMA.

These measured values may be used to determine various results of the advertising campaign. In particular embodiments, the measurement server computer may determine, based on the integrated measurement records, a change in prescription writing behavior that is associated with the consumer tokens and the HCP identifiers, and may further present the change in the analytics reports. Subsequently, through the optimization processes that have been described, the measurement server computer may automatically adjust one or more parameters of the DSP, for a particular campaign among the plurality of different campaigns, based on the change. As an example, if it is determined that purchasing impressions on a first website leads to a greater change in the prescription writing behavior than impressions on a second site, the DSP may automatically shift funding in the advertising campaign away from the first website in order to purchase more impressions on the second website. In particular embodiments, the measurement server computer may determine, based on the integrated measurement records, costs of each of the one or more measured campaigns, and in response, automatically signaling the DSP to change one or more configuration parameters to cause increasing spending on at least one of the measured campaigns having a lowest cost per prescription of the particular product. As an example, if it is determined that an impression on a first website generates conversions, and thus revenue, that is less than the cost of purchasing impressions on that first website (such that the advertising campaign is actually losing money by purchasing impressions on that first website), the DSP may automatically shift spending to focus more heavily on a second website where showing impressions results in more revenue than was spent on purchasing the impressions on that second website. In some embodiments, execution of optimization can comprise updating parameters to cause spending more on a specific campaign, a specific device, a specific time of day, on a specific publisher, or other attributes.

4. Implementation Examples 4.1 Computer System Overview

According to various embodiments, the techniques described herein are implemented by at least one computing device. The techniques may be implemented in whole or in part using a combination of at least one server computer and/or other computing devices that are coupled using a network, such as a packet data network. The computing devices may be hard-wired to perform the techniques, or may include digital electronic devices such as at least one application-specific integrated circuit (ASIC) or field programmable gate array (FPGA) that is persistently programmed to perform the techniques, or may include at least one general purpose hardware processor programmed to perform the techniques pursuant to program instructions in firmware, memory, other storage, or a combination. Such computing devices may also combine custom hard-wired logic, ASICs, or FPGAs with custom programming to accomplish the described techniques. The computing devices may be server computers, workstations, personal computers, portable computer systems, handheld devices, mobile computing devices, wearable devices, body mounted or implantable devices, smartphones, smart appliances, internetworking devices, autonomous or semi-autonomous devices such as robots or unmanned ground or aerial vehicles, any other electronic device that incorporates hard-wired and/or program logic to implement the described techniques, one or more virtual computing machines or instances in a data center, and/or a network of server computers and/or personal computers.

Figure 5:
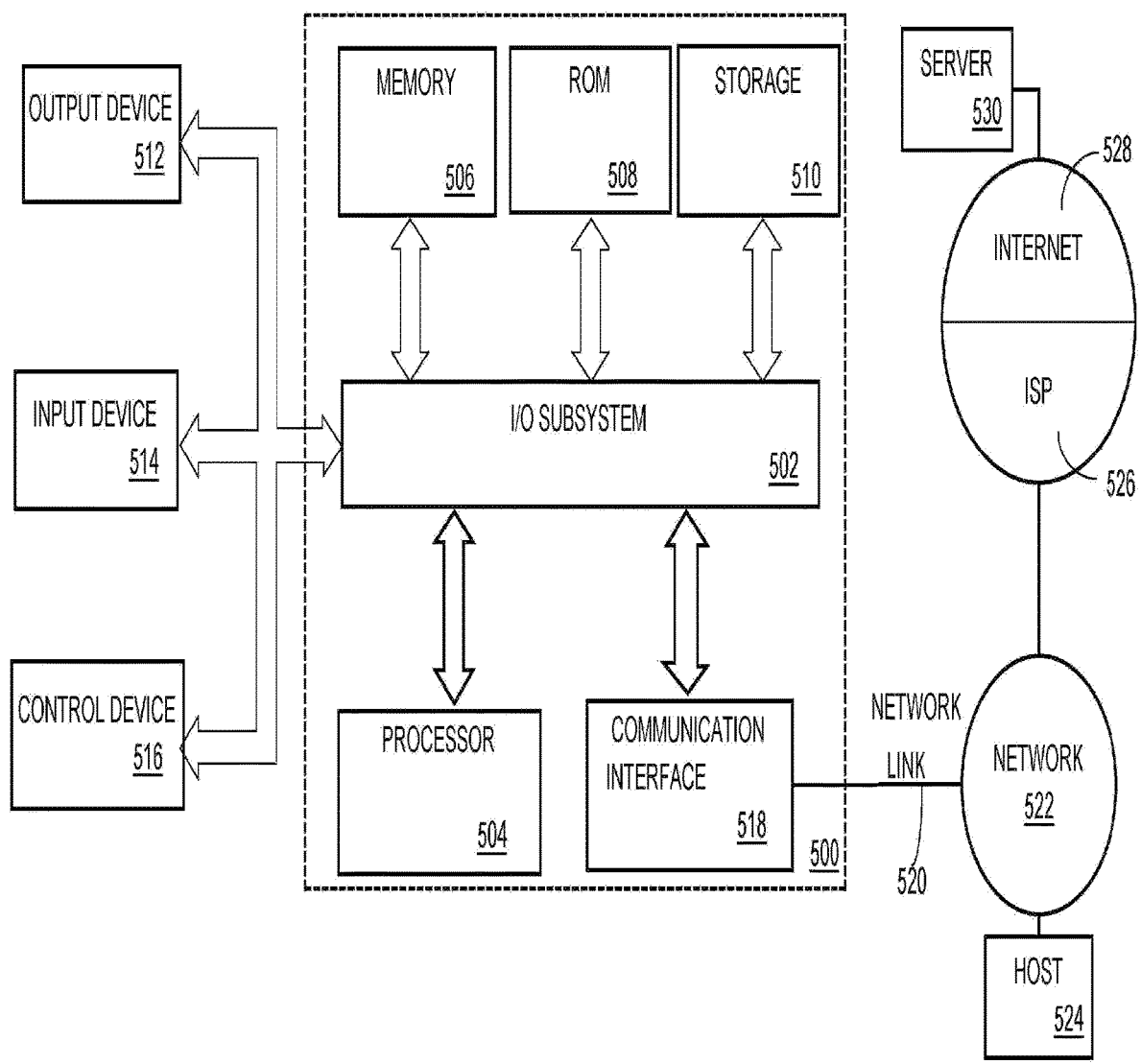
FIG. 5 is a block diagram that illustrates a computer system upon which an embodiment may be implemented.

FIG. 5 is a block diagram that illustrates an example computer system with which an embodiment may be implemented. In the example of FIG. 5, a computer system 500 and instructions for implementing the disclosed technologies in hardware, software, or a combination of hardware and software, are represented schematically, for example as boxes and circles, at the same level of detail that is commonly used by persons of ordinary skill in the art to which this disclosure pertains for communicating about computer architecture and computer systems implementations.

Computer system 500 includes an input/output (I/O) subsystem 502 which may include a bus and/or other communication mechanism(s) for communicating information and/or instructions between the components of the computer system 500 over electronic signal paths. The I/O subsystem 502 may include an I/O controller, a memory controller and at least one I/O port. The electronic signal paths are represented schematically in the drawings, for example as lines, unidirectional arrows, or bidirectional arrows.

At least one hardware processor 504 is coupled to I/O subsystem 502 for processing information and instructions. Hardware processor 504 may include, for example, a general-purpose microprocessor or microcontroller and/or a special-purpose microprocessor such as an embedded system or a graphics processing unit (GPU) or a digital signal processor or ARM processor. Processor 504 may comprise an integrated arithmetic logic unit (ALU) or may be coupled to a separate ALU.

Computer system 500 includes one or more units of memory 506, such as a main memory, which is coupled to I/O subsystem 502 for electronically digitally storing data and instructions to be executed by processor 504. Memory 506 may include volatile memory such as various forms of random-access memory (RAM) or other dynamic storage device. Memory 506 also may be used for storing temporary variables or other intermediate information during execution of instructions to be executed by processor 504. Such instructions, when stored in non-transitory computer-readable storage media accessible to processor 504, may render computer system 500 into a special-purpose machine that is customized to perform the operations specified in the instructions.

Computer system 500 further includes non-volatile memory such as read only memory (ROM) 508 or other static storage device coupled to I/O subsystem 502 for storing information and instructions for processor 504. The ROM 508 may include various forms of programmable ROM (PROM) such as erasable PROM (EPROM) or electrically erasable PROM (EEPROM). A unit of persistent storage 510 may include various forms of non-volatile RAM (NVRAM), such as FLASH memory, or solid-state storage, magnetic disk or optical disk such as CD-ROM or DVD-ROM and may be coupled to I/O subsystem 502 for storing information and instructions. Storage 510 is an example of a non-transitory computer-readable medium that may be used to store instructions and data which when executed by the processor 504 cause performing computer-implemented methods to execute the techniques herein.

The instructions in memory 506, ROM 508 or storage 510 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file processing instructions to interpret and render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. The instructions may implement a web server, web application server or web client. The instructions may be organized as a presentation layer, application layer and data storage layer such as a relational database system using structured query language (SQL) or no SQL, an object store, a graph database, a flat file system or other data storage.

Computer system 500 may be coupled via I/O subsystem 502 to at least one output device 512. In one embodiment, output device 512 is a digital computer display. Examples of a display that may be used in various embodiments include a touch screen display or a light-emitting diode (LED) display or a liquid crystal display (LCD) or an e-paper display. Computer system 500 may include other type(s) of output devices 512, alternatively or in addition to a display device. Examples of other output devices 512 include printers, ticket printers, plotters, projectors, sound cards or video cards, speakers, buzzers or piezoelectric devices or other audible devices, lamps or LED or LCD indicators, haptic devices, actuators or servos.

At least one input device 514 is coupled to I/O subsystem 502 for communicating signals, data, command selections or gestures to processor 504. Examples of input devices 514 include touch screens, microphones, still and video digital cameras, alphanumeric and other keys, keypads, keyboards, graphics tablets, image scanners, joysticks, clocks, switches, buttons, dials, slides, and/or various types of sensors such as force sensors, motion sensors, heat sensors, accelerometers, gyroscopes, and inertial measurement unit (IMU) sensors and/or various types of transceivers such as wireless, such as cellular or Wi-Fi, radio frequency (RF) or infrared (IR) transceivers and Global Positioning System (GPS) transceivers.

Another type of input device is a control device 516, which may perform cursor control or other automated control functions such as navigation in a graphical interface on a display screen, alternatively or in addition to input functions. Control device 516 may be a touchpad, a mouse, a trackball, or cursor direction keys for communicating direction information and command selections to processor 504 and for controlling cursor movement on display 512. The input device may have at least two degrees of freedom in two axes, a first axis (e.g., x) and a second axis (e.g., y), that allows the device to specify positions in a plane. Another type of input device is a wired, wireless, or optical control device such as a joystick, wand, console, steering wheel, pedal, gearshift mechanism or other type of control device. An input device 514 may include a combination of multiple different input devices, such as a video camera and a depth sensor.

In another embodiment, computer system 500 may comprise an internet of things (IoT) device in which one or more of the output device 512, input device 514, and control device 516 are omitted. Or, in such an embodiment, the input device 514 may comprise one or more cameras, motion detectors, thermometers, microphones, seismic detectors, other sensors or detectors, measurement devices or encoders and the output device 512 may comprise a special-purpose display such as a single-line LED or LCD display, one or more indicators, a display panel, a meter, a valve, a solenoid, an actuator or a servo.

When computer system 500 is a mobile computing device, input device 514 may comprise a global positioning system (GPS) receiver coupled to a GPS module that is capable of triangulating to a plurality of GPS satellites, determining and generating geo-location or position data such as latitude-longitude values for a geophysical location of the computer system 500. Output device 512 may include hardware, software, firmware and interfaces for generating position reporting packets, notifications, pulse or heartbeat signals, or other recurring data transmissions that specify a position of the computer system 500, alone or in combination with other application-specific data, directed toward host 524 or server 530.

Computer system 500 may implement the techniques described herein using customized hard-wired logic, at least one ASIC or FPGA, firmware and/or program instructions or logic which when loaded and used or executed in combination with the computer system causes or programs the computer system to operate as a special-purpose machine. According to one embodiment, the techniques herein are performed by computer system 500 in response to processor 504 executing at least one sequence of at least one instruction contained in main memory 506. Such instructions may be read into main memory 506 from another storage medium, such as storage 510. Execution of the sequences of instructions contained in main memory 506 causes processor 504 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage 510. Volatile media includes dynamic memory, such as memory 506. Common forms of storage media include, for example, a hard disk, solid state drive, flash drive, magnetic data storage medium, any optical or physical data storage medium, memory chip, or the like.

Storage media is distinct from but may be used in conjunction with transmission media. Transmission media participates in transferring information between storage media. For example, transmission media includes coaxial cables, copper wire and fiber optics, including the wires that comprise a bus of I/O subsystem 502. Transmission media may also take the form of acoustic or light waves, such as those generated during radio-wave and infra-red data communications.

Various forms of media may be involved in carrying at least one sequence of at least one instruction to processor 504 for execution. For example, the instructions may initially be carried on a magnetic disk or solid-state drive of a remote computer. The remote computer may load the instructions into its dynamic memory and send the instructions over a communication link such as a fiber optic or coaxial cable or telephone line using a modem. A modem or router local to computer system 500 may receive the data on the communication link and convert the data to be read by computer system 500. For instance, a receiver such as a radio frequency antenna or an infrared detector may receive the data carried in a wireless or optical signal and appropriate circuitry may provide the data to I/O subsystem 502 such as by placing the data on a bus. I/O subsystem 502 carries the data to memory 506, from which processor 504 retrieves and executes the instructions. The instructions received by memory 506 may optionally be stored on storage 510 either before or after execution by processor 504.

Computer system 500 also includes a communication interface 518 coupled to bus 502. Communication interface 518 provides a two-way data communication coupling to network link(s) 520 that are directly or indirectly connected to at least one communication networks, such as a network 522 or a public or private cloud on the Internet. For example, communication interface 518 may be an Ethernet networking interface, integrated-services digital network (ISDN) card, cable modem, satellite modem, or a modem to provide a data communication connection to a corresponding type of communications line, for example an Ethernet cable or a metal cable of any kind or a fiber-optic line or a telephone line. Network 522 broadly represents a local area network (LAN), wide-area network (WAN), campus network, internetwork or any combination thereof. Communication interface 518 may comprise a LAN card to provide a data communication connection to a compatible LAN, or a cellular radiotelephone interface that is wired to send or receive cellular data according to cellular radiotelephone wireless networking standards, or a satellite radio interface that is wired to send or receive digital data according to satellite wireless networking standards. In any such implementation, communication interface 518 sends and receives electrical, electromagnetic or optical signals over signal paths that carry digital data streams representing various types of information.

Network link 520 typically provides electrical, electromagnetic, or optical data communication directly or through at least one network to other data devices, using, for example, satellite, cellular, Wi-Fi, or BLUETOOTH technology. For example, network link 520 may provide a connection through a network 522 to a host computer 524.

Furthermore, network link 520 may provide a connection through network 522 or to other computing devices via internetworking devices and/or computers that are operated by an Internet Service Provider (ISP) 526. ISP 526 provides data communication services through a world-wide packet data communication network represented as internet 528. A server computer 530 may be coupled to internet 528. Server 530 broadly represents any computer, data center, virtual machine or virtual computing instance with or without a hypervisor, or computer executing a containerized program system such as DOCKER or KUBERNETES. Server 530 may represent an electronic digital service that is implemented using more than one computer or instance and that is accessed and used by transmitting web services requests, uniform resource locator (URL) strings with parameters in HTTP payloads, API calls, app services calls, or other service calls. Computer system 500 and server 530 may form elements of a distributed computing system that includes other computers, a processing cluster, server farm or other organization of computers that cooperate to perform tasks or execute applications or services. Server 530 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to interpret or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. Server 530 may comprise a web application server that hosts a presentation layer, application layer and data storage layer such as a relational database system using structured query language (SQL) or no SQL, an object store, a graph database, a flat file system or other data storage.

Computer system 500 may send messages and receive data and instructions, including program code, through the network(s), network link 520 and communication interface 518. In the Internet example, a server 530 might transmit a requested code for an application program through Internet 528, ISP 526, local network 522 and communication interface 518. The received code may be executed by processor 504 as it is received, and/or stored in storage 510, or other non-volatile storage for later execution.

The execution of instructions as described in this section may implement a process in the form of an instance of a computer program that is being executed and consisting of program code and its current activity. Depending on the operating system (OS), a process may be made up of multiple threads of execution that execute instructions concurrently. In this context, a computer program is a passive collection of instructions, while a process may be the actual execution of those instructions. Several processes may be associated with the same program; for example, opening up several instances of the same program often means more than one process is being executed. Multitasking may be implemented to allow multiple processes to share processor 504. While each processor 504 or core of the processor executes a single task at a time, computer system 500 may be programmed to implement multitasking to allow each processor to switch between tasks that are being executed without having to wait for each task to finish. In an embodiment, switches may be performed when tasks perform input/output operations, when a task indicates that it may be switched, or on hardware interrupts. Time-sharing may be implemented to allow fast response for interactive user applications by rapidly performing context switches to provide the appearance of concurrent execution of multiple processes simultaneously. In an embodiment, for security and reliability, an operating system may prevent direct communication between independent processes, providing strictly mediated and controlled inter-process communication functionality.

4.2 Artificial Neural Networks

Figure 10:
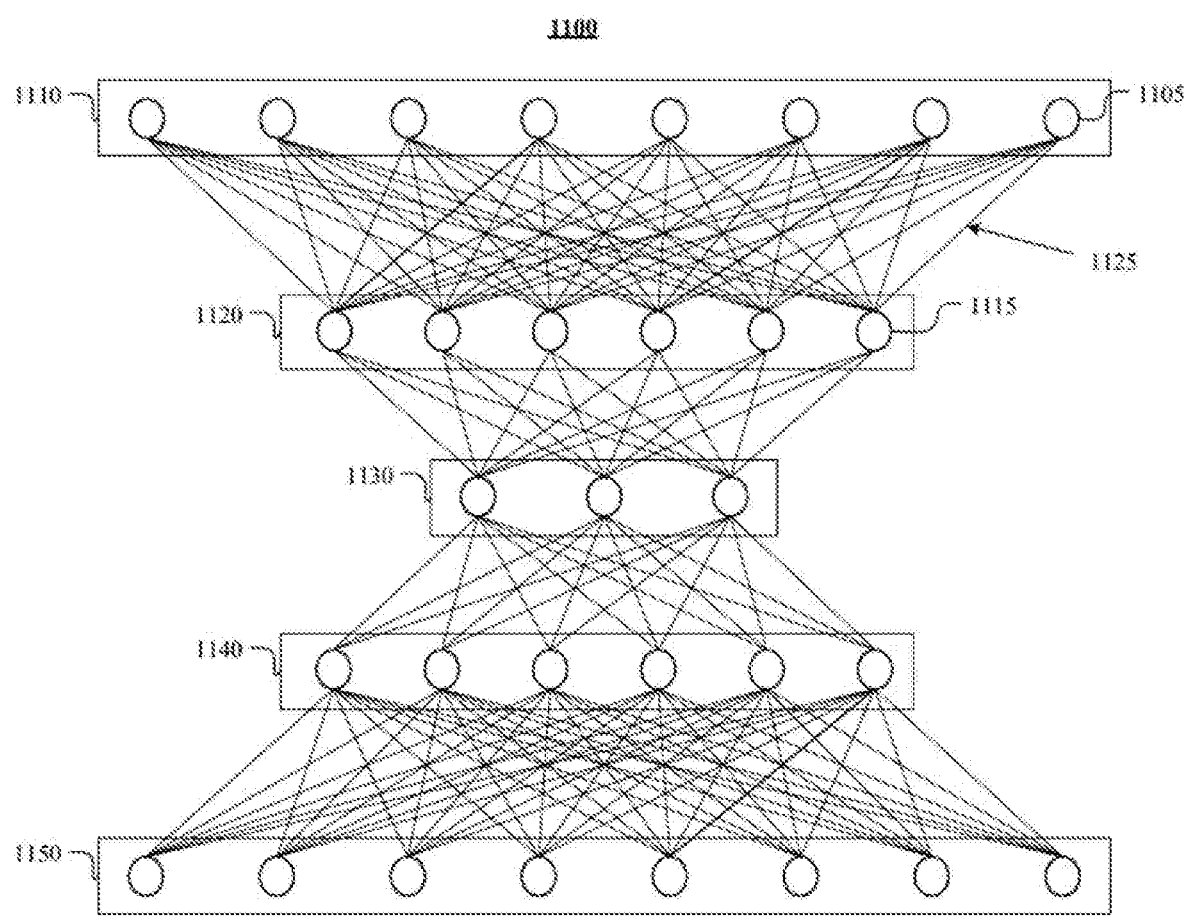
FIG. 10 illustrates an example artificial neural network.

FIG. 10 illustrates an example artificial neural network ("ANN") 1100. In particular embodiments, an ANN may refer to a computational model comprising one or more nodes. Example ANN 1100 may comprise an input layer 1110, hidden layers 1120, 1130, 1140, and an output layer 1150. Each layer of the ANN 1100 may comprise one or more nodes, such as a node 1105 or a node 1115. In particular embodiments, each node of an ANN may be connected to another node of the ANN. As an example and not by way of limitation, each node of the input layer 1110 may be connected to one of more nodes of the hidden layer 1120. In particular embodiments, one or more nodes may be a bias node (e.g., a node in a layer that is not connected to and does not receive input from any node in a previous layer). In particular embodiments, each node in each layer may be connected to one or more nodes of a previous or subsequent layer. Although FIG. 10 depicts a particular ANN with a particular number of layers, a particular number of nodes, and particular connections between nodes, this disclosure contemplates any suitable ANN with any suitable number of layers, any suitable number of nodes, and any suitable connections between nodes. As an example and not by way of limitation, although FIG. 10 depicts a connection between each node of the input layer 1110 and each node of the hidden layer 1120, one or more nodes of the input layer 1110 may not be connected to one or more nodes of the hidden layer 1120.

In particular embodiments, an ANN may be a feedforward ANN (e.g., an ANN with no cycles or loops where communication between nodes flows in one direction beginning with the input layer and proceeding to successive layers). As an example and not by way of limitation, the input to each node of the hidden layer 1120 may comprise the output of one or more nodes of the input layer 1110. As another example and not by way of limitation, the input to each node of the output layer 1150 may comprise the output of one or more nodes of the hidden layer 1140. In particular embodiments, an ANN may be a deep neural network (e.g., a neural network comprising at least two hidden layers). In particular embodiments, an ANN may be a deep residual network. A deep residual network may be a feedforward ANN comprising hidden layers organized into residual blocks. The input into each residual block after the first residual block may be a function of the output of the previous residual block and the input of the previous residual block. As an example and not by way of limitation, the input into residual block N may be F(x)+x, where F(x) may be the output of residual block N−1, x may be the input into residual block N−1. Although this disclosure describes a particular ANN, this disclosure contemplates any suitable ANN.

In particular embodiments, an activation function may correspond to each node of an ANN. An activation function of a node may define the output of a node for a given input. In particular embodiments, an input to a node may comprise a set of inputs. As an example and not by way of limitation, an activation function may be an identity function, a binary step function, a logistic function, or any other suitable function. As another example and not by way of limitation, an activation function for a node k may be the sigmoid function $$F_k(s_k) = \frac{1}{1 + e^{-s_k}},$$

the hyperbolic tangent function $$F_k(s_k) = \frac{e^{s_k} - e^{-s_k}}{e^{s_k} + e^{-s_k}},$$

the rectifier $F_k(s_k) = \max(0, s_k)$, or any other suitable function $F_k(s_k)$, where $s_k$ may be the effective input to node k. In particular embodiments, the input of an activation function corresponding to a node may be weighted. Each node may generate output using a corresponding activation function based on weighted inputs. In particular embodiments, each connection between nodes may be associated with a weight. As an example and not by way of limitation, a connection 1125 between the node 1105 and the node 1115 may have a weighting coefficient of 0.4, which may indicate that 0.4 multiplied by the output of the node 1105 is used as an input to the node 1115. As another example and not by way of limitation, the output $y_k$ of node k may be $y_k = F_k(s_k)$, where $F_k$ may be the activation function corresponding to node k, $s_k = \Sigma_j(w_{jk}x_j)$ may be the effective input to node k, $x_j$ may be the output of a node j connected to node k, and $w_{jk}$ may be the weighting coefficient between node j and node k. In particular embodiments, the input to nodes of the input layer may be based on a vector representing an object. Although this disclosure describes particular inputs to and outputs of nodes, this disclosure contemplates any suitable inputs to and outputs of nodes. Moreover, although this disclosure may describe particular connections and weights between nodes, this disclosure contemplates any suitable connections and weights between nodes.

In particular embodiments, an ANN may be trained using training data. As an example and not by way of limitation, training data may comprise inputs to the ANN 1100 and an expected output. As another example and not by way of limitation, training data may comprise vectors each representing a training object and an expected label for each training object. In particular embodiments, training an ANN may comprise modifying the weights associated with the connections between nodes of the ANN by optimizing an objective function. As an example and not by way of limitation, a training method may be used (e.g., the conjugate gradient method, the gradient descent method, the stochastic gradient descent) to backpropagate the sum-of-squares error measured as a distances between each vector representing a training object (e.g., using a cost function that minimizes the sum-of-squares error). In particular embodiments, an ANN may be trained using a dropout technique. As an example and not by way of limitation, one or more nodes may be temporarily omitted (e.g., receive no input and generate no output) while training. For each training object, one or more nodes of the ANN may have some probability of being omitted. The nodes that are omitted for a particular training object may be different than the nodes omitted for other training objects (e.g., the nodes may be temporarily omitted on an object-by-object basis). Although this disclosure describes training an ANN in a particular manner, this disclosure contemplates training an ANN in any suitable manner.

5. Extensions and Alternatives

In the foregoing specification, embodiments of the disclosure have been described with reference to numerous specific details that may vary from implementation to implementation. The specification and drawings are, accordingly, to be regarded in an illustrative rather than a restrictive sense. The sole and exclusive indicator of the scope of the disclosure, and what is intended by the applicants to be the scope of the disclosure, is the literal and equivalent scope of the set of claims that issue from this application, in the specific form in which such claims issue, including any subsequent correction.

What is claimed is:

1. A computer-implemented method comprising:
automatically executing, in a first iteration based upon a digitally stored execution schedule:
using a measurement server computer obtaining, from a demand-side platform (DSP), impression data specifying a first set of campaigns that are associated with a first set of one or more physicians, the first set of campaigns being among a plurality of different campaigns executed by the DSP;
using the measurement server computer, obtaining a plurality of records with healthcare provider (HCP) identifiers representing HCPs who have received digital impressions of the first set of campaigns that are associated with the first set of physicians;
using analytics instructions executing in a database server, accessing a database comprising de-identified tokenized claims data records, each of the data records relating to at least one claim concerning a prescription of a specified product and including at least one of the HCP identifiers;
using the analytics instructions, executing one or more database join operations on the claims data records and HCP identifiers to cause outputting a result set of one or more integrated measurement records specifying one or more measured goal campaigns among the plurality of different campaigns, the one or more measured goal campaigns being associated with the prescription of the specified product in at least one claims data record that is associated with at least one of the HCP identifiers;
receiving, at the measurement server computer, the integrated measurement records from the database server;
using the measurement server computer, generating and causing presenting one or more analytics reports based on the integrated measurement records; and
using the measurement server computer, executing a post call to the database server to register new campaign impression data to the database server; and
automatically executing the method in one or more second iterations based upon the digitally stored execution schedule and using the new campaign impression data.

2. The method of claim 1, further comprising determining, based on the integrated measurement records, a change in prescription writing behavior that is associated with one of the advertisements delivered on behalf of the measured goal campaign, the measured goal campaign being associated with the HCP identifiers, and presenting the change in the analytics reports.

3. The method of claim 1, further comprising training a machine learning model using a training dataset comprising features selected from the plurality of records and the de-identified tokenized claims data records to produce an optimization model, the machine learning model being trained to receive other integrated measurement records for other campaigns and to output predicted bid values for use in automatically adjusting one or more parameters of the DSP, for a target campaign among the plurality of different campaigns.

4. The method of claim 3, the optimization model comprising one of a random forest model, a neural network, a logistic regression, or a gradient boosted decision tree.

5. The method of claim 3, the training dataset further comprising other features selected from an attributes dataset comprising personal and demographics data associated with the consumers.

6. The method of claim 3, further comprising: using the optimization model, determining, based on the integrated measurement records, costs of each of the one or more measured campaigns, and in response, automatically signaling the DSP to change one or more configuration parameters to cause increasing spending on at least one of the measured campaigns having a lowest cost per prescription of the particular product.

7. The method of claim 3, further comprising: using the optimization model, receiving bid request data and an attributes dataset comprising personal and demographics data, and outputting predictions of bid values; updating a bidder of the DSP using the predictions of bid values output from the optimization model; serving one or more advertisements from the DSP based on the bidder having been updated.

8. The method of claim 1, wherein the generating and causing presenting of the one or more analytics reports comprises generating a data value indicating an elapsed time between a timestamp of a first digital impression associated with a particular campaign among the plurality of different campaigns and a first measured campaign of the particular campaign.

9. The method of claim 1, each campaign in the first set of campaigns being defined in the DSP using at least one clinical attribute, each clinical attribute comprising any of an ICD-10 code, CPT code, or NDC code.

10. The method of claim 1, wherein the HCP identifiers comprise any of National Practitioner Identifier (NPI) values and medical education (ME) values.

11. One or more non-transitory storage media storing instructions which, when executed by one or more measurement computing server devices, cause performance of a method, the method comprising:
automatically executing, in a first iteration based upon a digitally stored execution schedule:
using the measurement server computer obtaining, from a demand-side platform (DSP), impression data specifying a first set of campaigns that are associated with a first set of one or more physicians, the first set of campaigns being among a plurality of different campaigns executed by the DSP;
using the measurement server computer, obtaining a plurality of records with healthcare provider (HCP) identifiers representing HCPs who have received digital impressions of the first set of campaigns that are associated with the first set of physicians;
using analytics instructions executing in a database server, accessing a database comprising de-identified tokenized claims data records, each of the data records relating to at least one claim concerning a prescription of a specified product and including at least one of the HCP identifiers;
using the analytics instructions, executing one or more database join operations on the claims data records and HCP identifiers to cause outputting a result set of one or more integrated measurement records specifying one or more measured goal campaigns among the plurality of different campaigns, the one or more measured goal campaigns being associated with the prescription of the specified product in at least one claims data record that is associated with at least one of the HCP identifiers;

receiving, at the measurement server computer, the integrated measurement records from the database server;

using the measurement server computer, generating and causing presenting one or more analytics reports based on the integrated measurement records; and using the measurement server computer, executing a post call to the database server to register new campaign impression data to the database server; and automatically executing the method in one or more second iterations based upon the digitally stored execution schedule and using the new campaign impression data.

12. The media of claim 11, the method further comprising determining, based on the integrated measurement records, a change in prescription writing behavior that is associated with one of the advertisements delivered on behalf of the measured goal campaign, the measured goal campaign being associated with the HCP identifiers, and presenting the change in the analytics reports.

13. The media of claim 11, the method further comprising training a machine learning model using a training dataset comprising features selected from the plurality of records and the de-identified tokenized claims data records to produce an optimization model, the machine learning model being trained to receive other integrated measurement records for other campaigns and to output predicted bid values for use in automatically adjusting one or more parameters of the DSP, for a target campaign among the plurality of different campaigns.

14. The media of claim 13, the optimization model comprising one of a random forest model, a neural network, a logistic regression, or a gradient boosted decision tree.

15. The media of claim 13, the training dataset further comprising other features selected from an attributes dataset comprising personal and demographics data associated with the consumers.

16. The media of claim 13, the method further comprising: using the optimization model, determining, based on the integrated measurement records, costs of each of the one or more measured campaigns, and in response, automatically signaling the DSP to change one or more configuration parameters to cause increasing spending on at least one of the measured campaigns having a lowest cost per prescription of the particular product.

17. The media of claim 13, the method further comprising: using the optimization model, receiving bid request data and an attributes dataset comprising personal and demographics data, and outputting predictions of bid values; updating a bidder of the DSP using the predictions of bid values output from the optimization model; serving one or more advertisements from the DSP based on the bidder having been updated.

18. The media of claim 11, wherein the generating and causing presenting of the one or more analytics reports comprises generating a data value indicating an elapsed time between a timestamp of a first digital impression associated with a particular campaign among the plurality of different campaigns and a first measured campaign of the particular campaign.

19. The media of claim 11, each campaign in the first set of campaigns being defined in the DSP using at least one clinical attribute, each clinical attribute comprising any of an ICD-10 code, CPT code, or NDC code.

20. The media of claim 11, wherein the HCP identifiers comprise any of National Practitioner Identifier (NPI) values and medical education (ME) values.

* * * * *